(12) United States Patent
Kanayama et al.

(10) Patent No.: US 6,979,292 B2
(45) Date of Patent: *Dec. 27, 2005

(54) METHOD AND APPARATUS FOR FORMING AN IMAGE THAT SHOWS INFORMATION ABOUT A SUBJECT

(75) Inventors: Shoichi Kanayama, Koshigaya (JP); Kazuhiro Itsumi, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 104 days.

This patent is subject to a terminal disclaimer.

(21) Appl. No.: 10/628,446

(22) Filed: Jul. 29, 2003

(65) Prior Publication Data

US 2005/0004458 A1 Jan. 6, 2005

(30) Foreign Application Priority Data

Jul. 2, 2003 (JP) ............................ 2003-190336

(51) Int. Cl.[7] .............................................. A61B 8/00
(52) U.S. Cl. ..................................... 600/437; 600/443
(58) Field of Search ............................. 600/407–476, 600/479; 601/3, 4; 606/2, 3; 73/587, 596; 367/7

(56) References Cited

U.S. PATENT DOCUMENTS

| 5,713,356 | A | 2/1998 | Kruger |
| 5,840,023 | A | 11/1998 | Oraevsky et al. |
| 5,977,538 | A | 11/1999 | Unger et al. |
| 6,212,421 | B1 | 4/2001 | Vo-Dinh et al. |
| 2003/0069491 | A1 | 4/2003 | Kruger |

FOREIGN PATENT DOCUMENTS

WO WO 02/15776 2/2002

*Primary Examiner*—Ali Imam
(74) *Attorney, Agent, or Firm*—Oblon, Spivak, McClelland, Maier & Neustadt, P.C.

(57) ABSTRACT

An apparatus includes an optical transmission unit which irradiates a subject to be examined with light containing a specific wavelength component, an electroacoustic conversion unit which receives acoustic waves generated inside the subject by the light radiated by the optical transmission unit and converts them into electrical signals, an image data generating unit which generates first image data on the basis of the reception signals obtained by the electroacoustic conversion unit, an electroacoustic conversion unit which receives ultrasonic reflection signals obtained by transmitting ultrasonic waves to the subject and converts them into electrical signals, an image data generating unit which generates second image data on the basis of the reception signals obtained by the electroacoustic conversion unit, and a display unit which combines the first and second image data and displays the resultant data.

43 Claims, 18 Drawing Sheets

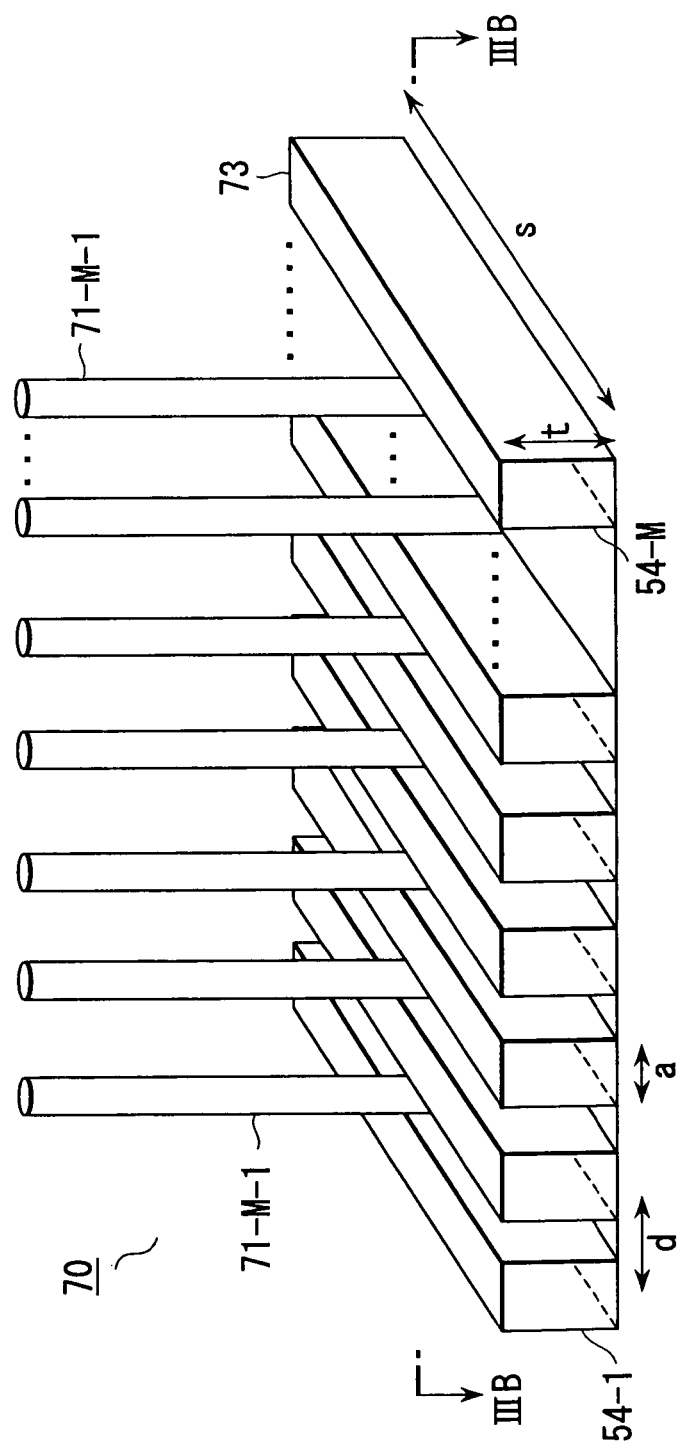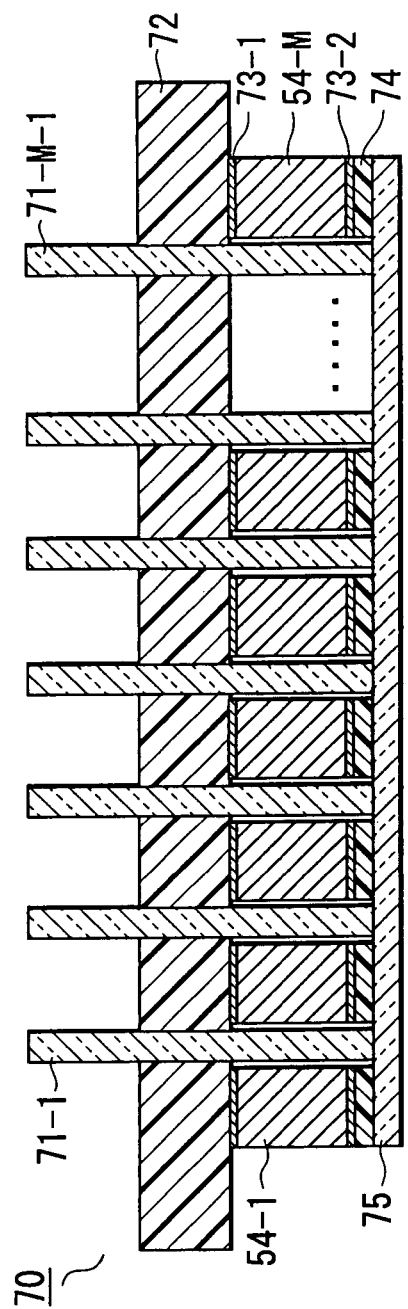
FIG. 3A
FIG. 3B

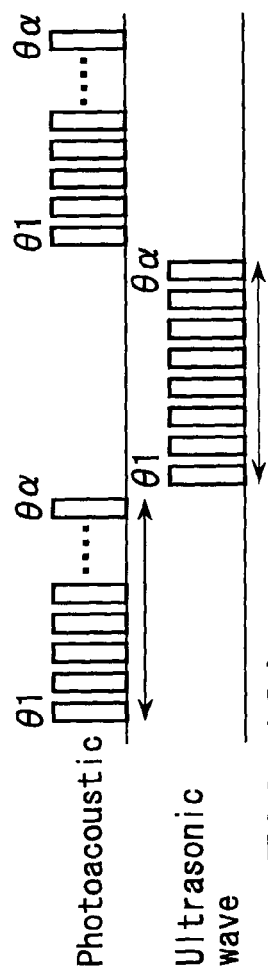
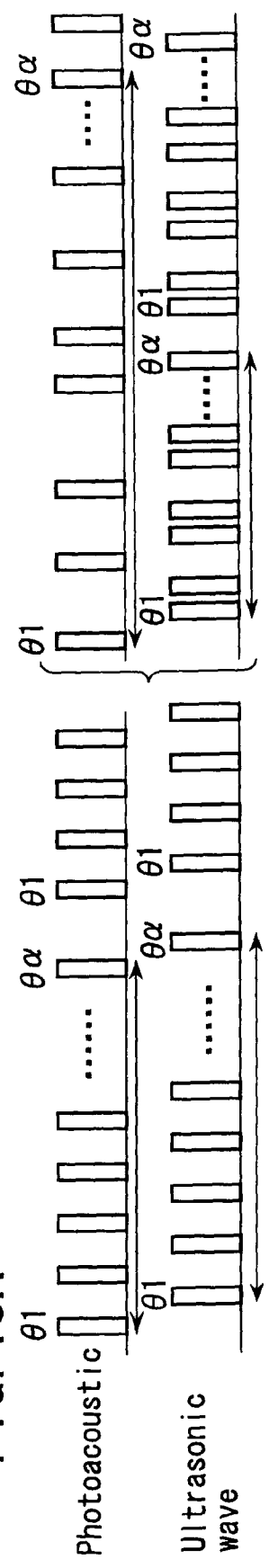
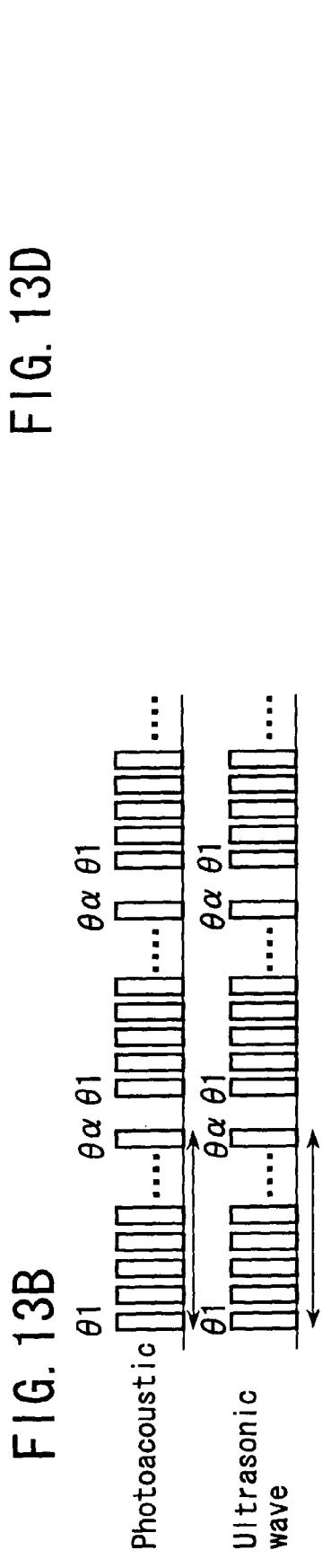
FIG. 13A
FIG. 13B
FIG. 13C
FIG. 13D

[Single-mode fiber
Tape thickness: 0.3mm
Tape width: 6.3mm]

Scanning direction

METHOD AND APPARATUS FOR FORMING AN IMAGE THAT SHOWS INFORMATION ABOUT A SUBJECT

CROSS-REFERENCE TO RELATED APPLICATIONS

This application is based upon and claims the benefit of priority from the prior Japanese Patent Application No. 2003-190336, filed Jul. 2, 2003, the entire contents of which are incorporated herein by reference.

BACKGROUND OF THE INVENTION

1. Field of the Invention

The present invention relates to a method and apparatus for aquiring and superimposing two acoustic images, one generated from the energy of light radiated into a subject being examined and the second is an ultrasound echo image generated from ultrasonic waves directed into the subject being examined superposition of the two images yields a distribution of substance concentration with respect to morphological features in the subject's tissue.

2. Description of the Related Art

A method of acquiring information about a subject has been used to measure the concentration of a component contained in a body fluid such as blood, other body fluids in the subject or excised tissue, thereby to achieve accurate diagnosis, fast determination of treatment course, and improved healthcare. To measure the concentration of each component of a body fluid, the body fluid must be extracted from the subject by blood collection. The extraction of the fluid is painful. It damages the skin of the subject and introduces the possibility of biohazard contamination to the subject and the operator.

To solve this problem, a number of patents and journal articles describe non-invasive methods of acquiring information about analyte concentration in the tissue of human subjects. One of the methods is "photoacoustic spectroscopy". In the photoacoustic spectroscopy, the concentration of a specific substance, such as glucose or hemoglobin, contained in the blood of a subject is quantitatively determined from the acoustic waves that are generated when the subject's tissue is irradiated with short duration pulses of light of a predetermined wavelength. U.S. Pat. No. 5,348, 002, WO9838904A1, WO0215776A1 describe methods for the non-invasive determination of substances in human tissue using photoacoustic measurements. The light may be visible light, infrared light, or intermediate infrared light.

In addition to hemoglobin and glucose, photoacoustic spectroscopy can be used to determine other analytes in human tissue such as cholesterol, natural fat, bilirubin, collagen, and the like. Diagnosis of cutaneous cancer or breast cancer based on the results of the photoacoustic spectroscopy has recently proven its clinical usefulness. The photoacoustic spectroscopy utilizes a suitable substance selected from these substances and light having a wavelength at the substance selected exhibits highest absorption. Further it is increasingly expected that a diagnosis method be invented, which provides a two-dimensional image representing the concentration distribution of these substance.

While photoacoustic spectroscopy is used to measure substance concentration in tissue, ultrasound imaging has been extensively used for determination of the presence of morphological features, such as cysts and lumps, in human organs. Combining the distribution of substances and the morphological features in human tissue leads to better diagnosis and improved healthcare as it provides better characterization of the tissue, more accurate diagnosis for malignancies, and better definition of regions of abnormal pathology to guide in surgical removal of these regions.

Breast cancer is a major source of mortality in females. Screening for and early diagnosis of breast cancer is of tremendous value in cutting mortality rate and in health care cost containment. Current methods involve manual examination of breast tissue for unusual lumps and routine mammography to look for suspicious lesions. In a mammogram is deemed suspicious, it is followed by ultrasound imaging, and surgical biopsy. These set of steps take considerable time before reaching a final conclusion.

Non-invasive optical techniques offer the opportunity for determining blood vessel distribution in tissue, thus locating a potential tumor by the presence of abnormal vascularization in a tissue region. Non-invasive optical techniques include time resolved light propagation in tissue. Another method is the measurement of the change in modulation and phase angle as photon density wave propagate in the tissue. These are presented is several journal articles (B. Chance "Near-infrared images using continuous, phase-modulated, and pulsed light with quantitation of blood and blood oxygenation' in Advances in Optical Biopsy and Optical Mammography, R. Alfano ed, Annals of the New York Academy of Sciences 1998; Volume 838: pages 29–45; by S. Fantini et al "Frequency domain optical mammography: Edge effect corrections" Medical Physics 1996; Volume 23: pages 1–6, and by M. A. Franceschini et al "Frequency Domain techniques enhance optical mammography; initial clinical results" Proceedings of the National Academy of Sciences USA 1997; Volume 94: pages 6468–6473 (1997)). These methods suffer from imprecision of image conversion and image distortions close to the edges of the body part, such as the breast.

Imaging methods of the art that includes ultrasound, CAT scan, X-ray and MRI describe the morphology of the body part, in this case the breast without indicating the distribution of hemoglobin. Further, MRI and CAT scan have large expensive equipment that cannot be transformed easily.

A diagnostic method and apparatus that utilizes the morphological image and the distribution of subatances in the morphological feature leads to better diagnosis. Use of photoacoustic imaging to determine analyte distribution in breast tissue was described by A. A. Oraevsky et al "Laser opto-acoustic imaging of breast: Detection of cancer angiogenesis" SPIE Proceedings 1999; Volume 3597, pages: 352–363; and A. A. Oraevsky et al "Opto-acoustic imaging of blood for visualization and diagnostics of breast cancer" SPIE Proceedings 2002; Volume 4618, pages: 81–94. It is also described in the patent art in U.S. Pat. No. 5,840,023 "Optoacoustic imaging for medical diagnosis", WO 01/10295 "Photoacoustic monitoring of blood oxygenation", and U.S. Pat. No. 6,309,352 B1 "Real Time optoacoustic monitoring of changes in tissue properties".

Oraevsky et al use photoacoustic imaging alone without combination with ultrasound imaging. They do not teach combination of photoacoustic and ultrasound images that are detected using co-registered ultrasound transducers. The method leads to the possibility of distortion of the vascular image due to effect of the morphological features on tissue bulk modulus.

Other application of optical methods to generate an image of analyte distribution in tissue is described by Q. Zhu et al in "Combined ultrasound and optical tomography imaging" SPIE Proceedings 1999; Volume 3579, pages: 364–370; and Q. Zhu et al "Optical imaging as an adjunct to ultrasound in differentiating benign from malignant lesions" SPIE Proceedings 1999; Volume 3579: pages 532–539. Zhu et al uses ultrasound imaging to define the morphological features in tissue and then apply frequency domain imaging to determine vascularization i.e. hemoglobin distribution. Optical fibers and photomultiplier tubes are used as detectors for the optical method and ultrasound transducers are used for ultrasound imaging with less optimum co-registration between the vascularization and the morphological images. Does not teach combination of photoacoustic and ultrasound images that are detected using co-registered ultrasound transducers.

In a conventional non-invasive method of measuring glucose, the skin of the subject is irradiated with near-infrared light beams of different wavelengths. The glucose concentration is measured by arithmetically processing the acoustic waves obtained (see Jpn. Pat. Appln. KOKAI Publications Nos. 3-47099 and 5-58735).

The conventional photoacoustic spectroscopy uses a microphone and a piezoelectric element made of lead zirconate titanate (PZT) ceramics, or the like, to detect acoustic waves (see Jpn. Pat. Appln. KOKAI Publications Nos. 10-189 and 11-235331).

Research has been conducted on imaging methods using the photoacoustic effect for diagnosing breast cancer (see Jpn. Pat. Appln. KOKAI Publications Nos. 3-47099). FIG. 13 illustrates the system 100 for acquiring photoacoustic image data, described in non-patent reference 1. The system 100 comprises a laser generator 101, an optical fiber 103, an array of electroacoustic transducer elements 104, and a computer system 105. The laser generator 101 generates light pulses. The optical fiber 103 guides the light pulse to the breast 102 of a subject to be examined. The electroacoustic transducer elements 104 are placed, facing the optical fiber 103. Each element 104 has a concaved surface. The computer system 105 controls transmission of optical pulses, acquires acoustic waves, and reconstructs an image.

The subject lies on a table, with the breast 102 positioned between the optical fiber 103 and the array of electroacoustic transducer elements 104. Then, the tissues in the breast 102 are irradiated with light (laser beam) applied from the optical fiber 103. The blood components in the internal tissues generate acoustic waves. The electroacoustic transducer elements 104 receive the acoustic waves.

In this method, the concentration of hemoglobin in blood, for example, can be measured with higher sensitivity than the concentration of any other substance components, by virtue of the photoacoustic effect based on a predetermined wavelength. Therefore, a photoacoustic image of a tumor tissue in the breast can be more readily detected than an image obtained by an ultrasonic diagnosis apparatus, X-ray apparatus, MRI apparatus, or the like, which has hitherto been used. This is because vascularization, which is the number of blood vessels, and the blood flow rate are higher in the tumor tissue than in normal tissues, in order to accommodate the higher metabolic activity in the tumor. Increased vascularization occurs through generation of more blood vessels in the tumor and its surroundings. Generation of new blood vessels in tumors is known as angiogenesesis.

The methods disclosed in Jpn. Pat. Appln. KOKOKU Publication Nos. 3-47099 and 5-58735, and Jpn. Pat. Appln. KOKAI Publication Nos. 10-189 and 11-235331 are designed to measure the concentration of a specific substance in a local region. However, none of these publications teaches techniques of providing an image showing concentration distributions.

The method described in A. A. Oraevsky, et al., "Laser optoacoustic imaging of breast cancer in vivo", Proc. SPIE, Vol. 4256: pages. 6–15, 2001, lacks operability. This is because, the optical fiber 103 and an array of electroacoustic transducer elements 104 opposite to each other, and the subject lies with the breast 102 held between them. It is desirable to form the optical fiber 103 integral with the array of electroacoustic transducer elements 104, because air must be expelled, as much as possible, from the gap between the array and the subject, particularly when an image is reconstructed from the acoustic waves generating from inside the subject.

In addition, image reconstruction using such acoustic waves (referred to as "photoacoustic imaging method" hereinafter) is performed only for a particular component such as hemoglobin. Hence, no signals can be obtained from any region than contain without the component. Therefore, when the photoacoustic imaging method is performed to examine the breast for cancer as described in A. Oraevsky et al., "Laser optoacoustic imaging of breast cancer", it is difficult to determine an accurate positional relationship between a tumor and morphological features in the tissue and such as healthy mammary gland tissue surrounding it.

Thus there is a need to develop methods and apparatus for diagnosing disease states by combining imaging of morphological features and distribution of substance concentration within the features, while avoiding image distortion, incorporating common body interface and common detectors, for the imaging measurement and the substance distribution measurement. The method and the apparatus should lead to applying the same pressure, same air gaps, same interfaces for the imaging measurement and the substance distribution measurement. The purpose of this invention is to fulfill this need.

BRIEF SUMMARY OF THE INVENTION

The present invention has been made in view of the foregoing. An object of the invention is to provide an apparatus for forming an image that provides information about a subject being examined. The apparatus has a data acquisition system easy to operate to form an image showing information about the subject, by using the photoacoustic effect inside the living body, and which can generate data representing an image having high contrast resolution and high spatial resolution.

To achieve the object, an apparatus according to this invention comprises a light generating unit, irradiation unit, waveguide means, first electroacoustic conversion means, first image data generating means, ultrasonic wave transmission means, second electroacoustic conversion means, second image data generating means, and display means. The light-generating unit generates light containing a specific wavelength component. The irradiation unit radiates the light generated by the light-generating unit into a subject to be examined. The waveguide means guides the light generated by the light-generating unit to the irradiation unit. The first electroacoustic conversion means converts acoustic waves generated in the subject by the light radiated by the irradiation unit into electrical signals by using a plurality of arrayed electroacoustic transducer elements. The first image data generating means generates first image data on the basis of the signals obtained by the first electroacoustic conversion means. The ultrasonic wave transmission means transmits ultrasonic waves into the subject. The second electroacoustic conversion means converts components of the ultrasonic waves transmitted by the ultrasonic wave transmission means and reflected inside the subject into electrical signals, by using a plurality of arrayed electroacoustic transducer elements. The second image data generating means generates second image data from the signals generated by the second electroacoustic conversion means. The display means displays the first image data and the second image data.

The present invention provides a method for the determination of the distribution of a substance in human tissue and superimposing this distribution on a morphological image on the body part under examination to yield better diagnosis. The method utilized common body interface and common detectors, with the light sources interposed between the detectors in one structure. Same pressure applies, same air gaps, same interfaces to minimize image distortion.

The present invention also provides an apparatus that can display a photoacoustic image and ultrasound image of almost the same region of a tissue being examined, and is very easy to operate because the same photoacoustic detectors used are sound conversion elements, which can receive photo-generated acoustic waves, can also transmit and receive ultrasonic waves.

Additional objects and advantages of the present invention will be set forth in the description which follows, and in part will be obvious from the description, or may be learned by practice of the present invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the present invention and, together with the general description given above and the detailed description of the preferred embodiments given below, serve to explain the principles of the present invention.

FIGS. 3A and 3B are views of an applicator according to the first embodiment of the present invention;

FIGS. 13A to 13D are timing charts explaining the scanning performed in a photoacoustic imaging method and pulse echo method, both according to the fifth embodiment of the invention;

DETAILED DESCRIPTION OF THE INVENTION

Figure 1:
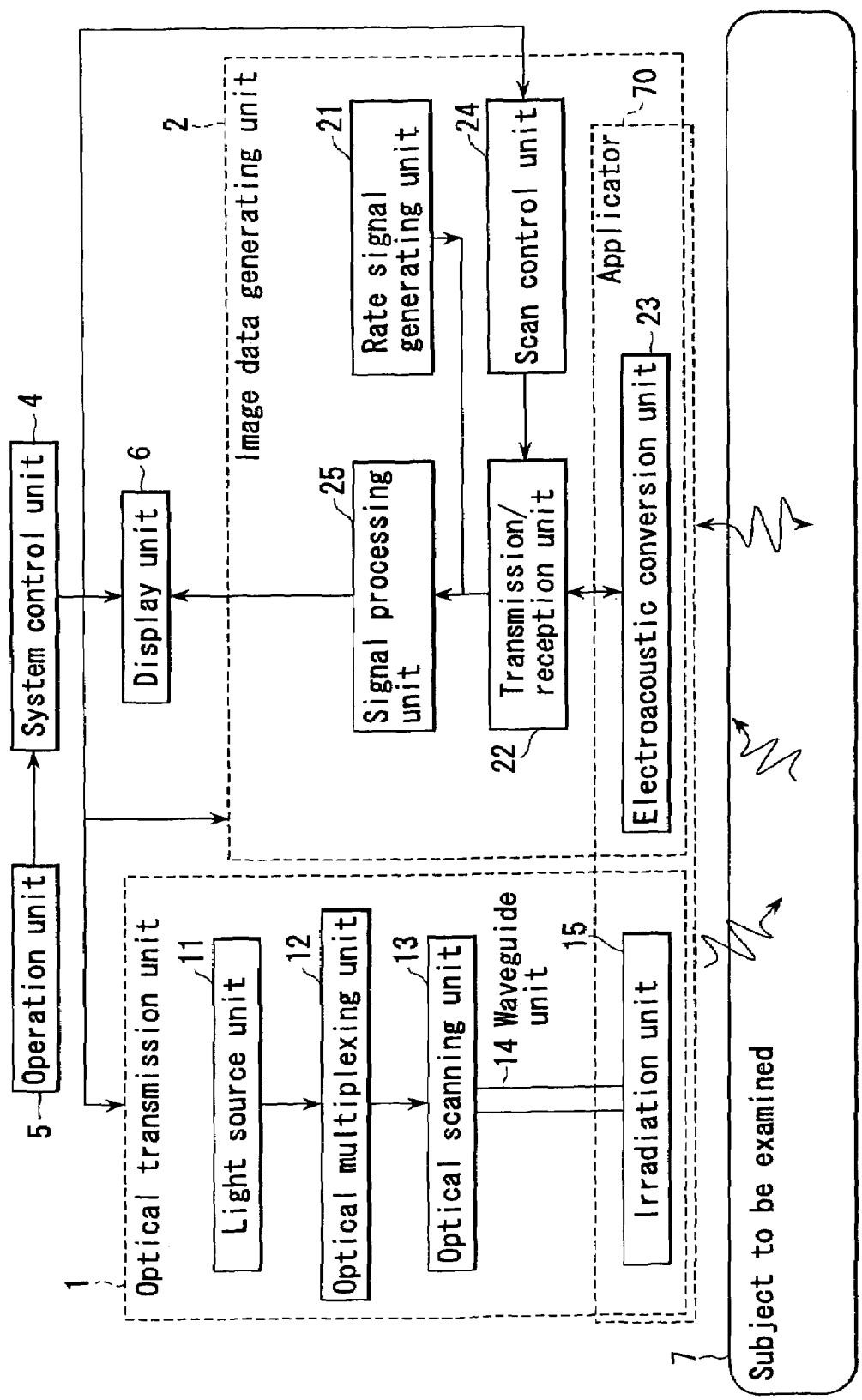
FIG. 1 is a block diagram of a subject-information imaging apparatus according to the first embodiment of the invention.

One aspect of this invention is a method for the determination of the distribution of an analyte concentration in human tissue and superimposing this distribution on a morphological image of the body part under examination to yield better diagnosis.

One aspect of this invention is a method for diagnosing breast cancer in humans that comprises the steps of:

a) bringing a diagnostic probe in touch with breast tissue, the diagnostic probe further comprises an ultrasound imaging elements and photoacoustic illumination and detection elements, b) illuminating said breast tissue with short duration light pulses having wavelengths that lie in the absorption spectral bands of hemoglobin, to generate photoacoustic signals, c) detecting said photoacoustic signal using ultrasound transducers to determine the distribution of blood vascularization in breast tissue, d) Simultaneously or sequentially, generating and detecting an ultrasound image of the morphology of said human breast tissue, using ultrasound transducers that are co-registered with said photoacoustic detection transducers used in the detection of said photoacoustic signals, e) overlaying said photoacoustic hemoglobin distribution image over said ultrasound morphology image to generate a combined image of the vascular distribution in different morphological structures in the breast, said morphological structure are the lesions of interest; and establishing a probability of diagnosis based on said distribution of vascularization on said lesions.

The method and apparatus of this invention can be used to determine the concentration of chemotherapeutic agents in normal and malignant human tissue, thus offering a method for tracking the potential effectiveness of the therapy. One such class of therapeutic agents, are those used in photodynamic therapy. Thus, in addition in assisting in better and more accurate diagnosis, the method and apparatus of this invention can be used to direct treatment.

The wavelengths of light are in the long wavelength visible and near infrared spectral range than can penetrate deeply enough in tissue without significant absorption by tissue water and tissue pigments. A preferred spectral range is between 530 nm and 1300 nm.

The photo acoustic detection elements and the ultrasound detection elements used in the method and apparatus of this invention are common. This allows for maximum co-registration between the two images and minimized variation in detector-body interface between the two imaging methods.

The ultrasound transducers are piezoelectric elements, such as piezo electric ceramics, or polymer films such as polyvinylpyrrolidine floride. A preferred material is PZNT (lead-zirconium-niobium-titanium) single crystal.

Another aspect of this invention is an apparatus for determination of the concentration of a substance such as hemoglobin on tissue morphological features such as lumps and lesions for generation better diagnosis of disease such as breast cancer in humans, this apparatus comprises:

a. light generating unit, which generates light containing a specific wavelength component;

b. an irradiation unit, which radiates the light generated by the light-generating unit into a subject to be examined;

c. wave guide means for guiding the light generated by the light-generating unit to the irradiation unit;

d. first electroacoustic conversion means for converting acoustic waves generated in the subject by the light radiated by the irradiation unit into electrical signals by using a plurality of arrayed electroacoustic transducer elements;

e. first image data generating means for generating first image data on the basis of the signals obtained by the first electroacoustic conversion means;

f. ultrasonic wave transmission means for transmitting ultrasonic waves into the subject;

g. second electroacoustic conversion means for converting components of the ultrasonic waves transmitted by the ultrasonic wave transmission means, which are reflected inside the subject into electrical signals by using a plurality of arrayed electroacoustic transducer elements;

h. second image data generating means for generating second image data on the basis of the signals obtained by the second electroacoustic conversion means; and i. display means for displaying the first image data and the second image data.

In its generalized application as subject-information imaging apparatus, several aspects of the apparatus of this invention is described in the following eight embodiments.

First Embodiment:

The first embodiment of the present invention will be described, with reference to FIGS. 1 to 6.

The first embodiment is a subject-information imaging apparatus that can form an image showing a hemoglobin distribution in the subject, which will be used to diagnose breast cancer. The apparatus is characterized in that the electroacoustic conversion unit is integrally formed with the irradiation unit. That is, the optical fibers of the irradiation unit have their output ends held between the electroacoustic transducer elements arrayed in the electroacoustic conversion unit. The apparatus can perform a photoacoustic imaging method and a conventional pulse echo method, by using this electroacoustic conversion unit, to combine and display the image data items obtained from the same region in the subject.

Hereinafter, the sound waves generated by the photoacoustic imaging method will be referred to as "acoustic waves" and the sound waves transmitted/received by the general pulse echo method will be referred to as ultrasonic waves".

Figure 2:
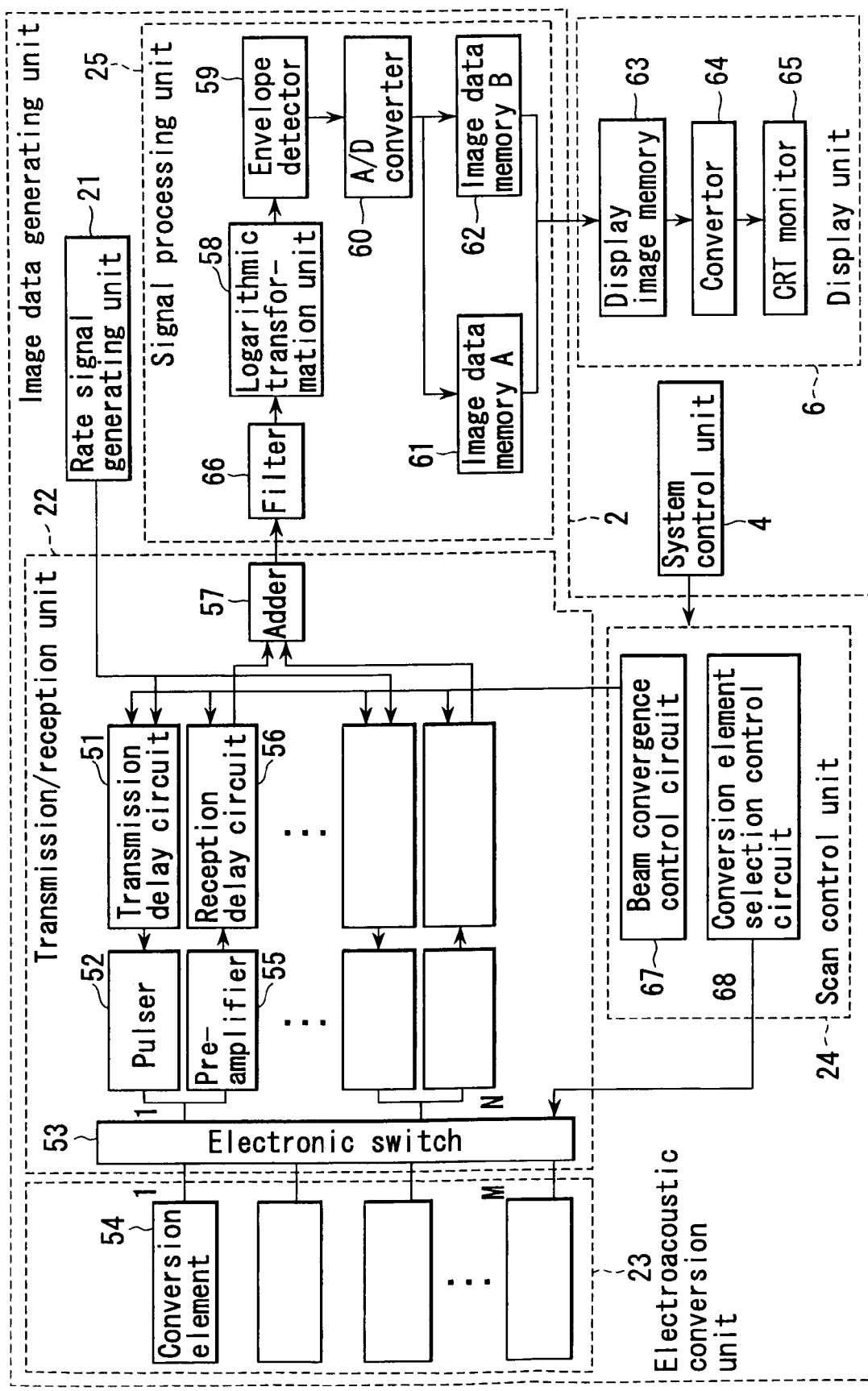
FIG. 2 is a block diagram of the image data generating unit of the apparatus according to the first embodiment of the invention.

The subject-information imaging apparatus according to the first embodiment will be described with reference to FIGS. 1 and 2. FIG. 1 is a block diagram of the subject-information imaging apparatus according to the first embodiment. FIG. 2 is a block diagram showing the image data generating unit 2 provided in the subject-information imaging apparatus.

The subject-information imaging apparatus comprises an optical transmission unit 1, image data generating unit 2, system control unit 4, operation unit 5, display unit 6, and image data generating unit 20. The optical transmission unit 1 irradiates a subject 7 with light having a predetermined wavelength, causing the subject 7 to generate acoustic waves. The image data-generating unit 2 generates ultrasonic image data and photoacoustic image data from the acoustic waves the subject 7 has generated. The display unit 6 displays the photoacoustic image data and ultrasonic image data. By using the operation unit 5, the operator inputs patient information and imaging conditions for the apparatus. The system control unit 4, controls the respective units 1, 2, 5, 6 and 20.

The optical transmission unit 1 has a light source unit 11, an optical multiplexing unit 12, an optical scanning unit 13, a multi-channel waveguide unit 14, and an irradiation unit 15. The light source unit 11 has a plurality of light sources of different wavelengths. The optical multiplexing unit 12 multiplexes light beams having different wavelengths on the same optical axis. The multi-channel waveguide unit 14 guides this light onto the skin of the subject 7. The optical scanning unit 13 scans the subject 7, while switching channels to be used in the waveguide unit 14. The irradiation unit 15 irradiates the subject 7 with the light applied through the waveguide unit 14.

The light source unit 11 has a plurality of light sources, which generate light beams of different wavelengths. Each light source is a light-emitting element such as a semiconductor laser (LD), light-emitting diode (LED), solid-state laser or gas laser, which generates a specific wavelength component or monochromatic light containing it. To measure the hemoglobin concentration in the subject 7, either an Nd:YAG laser (solid-state laser) having a wavelength of about 1,000 nm or an He—Ne gas laser with a wavelength of 633 nm is used to generate a laser beam having a pulse width of about 10 nsec. Although hemoglobin in a living body varies in optical absorption, depending on its type (oxyhemoglobin, deoxyhemoglobin, methemoglobin, carbaminohemoglobin, or the like), it generally absorbs light in the range of 600 nm to 1,000 nm. A compact light-emitting element, such as an LD or LED, may be used, which is made of InGaAlP for an emission wavelength of about 550 to 650 nm; GaAlAs for an emission wavelength of about 650 to 900 nm; or InGaAs or InGaAsP for an emission wavelength of about 900 to 2,300 nm. Recently, a light-emitting element made of InGaN, which emits light with a wavelength of 550 nm or less, has come into use. Alternatively, an OPO (Optical Parametrical Oscillator) laser, which is tunable laser using nonlinear optical crystal, may be used.

The optical multiplexing unit 12 is designed to multiplex light beams with different wavelengths emitted from a plurality of light sources on the same optical axis. A collimator lens converts the light beams into parallel light beams. A right-angled prism or dichroic mirror aligns the optical axes of the light beams. The collimator lens and the prism or mirror constitute a relatively compact multiplexing optical system. The system may be replaced by a commercially available multiple multiplexer/demultiplexer that has been developed for optical communication. If the light source unit 11 is the above-mentioned OPO laser that can continuously change wavelength, the optical multiplexing unit 12 need not be used.

The waveguide unit 14 guides the light output from the optical multiplexing unit 12 to the subject 7. An optical fiber or optical thin film waveguide is utilized for efficient optical propagation. Instead, free space propagation can also be employed. In the first embodiment of the invention, the waveguide unit 14 comprises a plurality of optical fibers 71 (to be described later). Light is applied through one optical fiber selected from these optical fibers 71.

The optical scanning unit 13 optically scans the subject 7 by sequentially selecting the plurality of optical fibers 71 arrayed in the waveguide unit 14.

The irradiation unit 15 is located on the output end of the waveguide unit 14. The unit 15 is integrated with an electroacoustic conversion unit 23 (described later). For example, the output end portions of the optical fibers 71 in the irradiation unit 15 are positioned adjacent to arrayed conversion elements 54 that constitute the electroacoustic conversion unit 23.

The image data generating unit 2 of the subject-information imaging apparatus includes, in addition to the electroacoustic conversion unit 23, a transmission/reception unit 22, a scan control unit 24, a rate signal generating unit 21, and a signal processing unit 25. The electroacoustic conversion unit 23 converts acoustic and electrical signals. The transmission/reception unit 22 selectively drives the electroacoustic conversion unit 23, and selectively receives reception signals from the electroacoustic conversion unit 23, while delaying transmission/reception signals by predetermined time, thereby performing phased addition. The scan control unit 24 controls the selective operation of the electroacoustic conversion unit 23 and the delay time given by the transmission/reception unit 22. The rate signal generating unit 21 outputs a rate pulse for setting the repeating period of transmission ultrasonic waves to be radiated into the subject 7. The signal processing unit 25 performs various processes on the signals received from the transmission/reception unit 22.

The electroacoustic conversion unit 23 has M small conversion elements 54 arrayed in a line on its distal end portion. The distal end portion contacts the body surface of the subject 7 to transmit and receive acoustic and ultrasonic waves. The conversion element 54 can convert an electrical driving pulse into a transmission ultrasonic wave at the time of transmission. It can convert an acoustic wave or received ultrasonic wave, too, into an electrical signal at the time of reception. The electroacoustic conversion unit 23, generally known as "ultrasonic probe", has a compact and light body. It is connected to the transmission/reception unit 22 by a multi-channel cable (to be described later). The electroacoustic conversion unit 23 may be a sector scan unit, linear unit, or convex scan unit, depending on which region should be diagnosed. In this embodiment, the unit 23 is a linear scan unit.

As FIG. 2 shows, the transmission/reception unit 22 includes transmission delay circuits 51, pulsers 52, electronic switch 53, preamplifiers 55, reception delay circuits 56, and adder 57.

The transmission delay circuits 51 are designed to set the convergence distances of transmission ultrasonic waves at the time of transmission. The circuits 51 impart, to the rate pulse output from the rate signal generating unit 21, the timings of driving the N' conversion elements 54 selected from the M (M>N') conversion elements 54 of the electroacoustic conversion unit 23. The circuits 51 supply the rate pulses to the pulsers 52.

The pulsers 52 are driving circuits which generate high-voltage pulses for driving the N' conversion elements 54. These circuits generate impulses having peak values of several hundred volts by using output signals from the transmission delay circuits 51 as trigger signals.

The electronic switch 53 selects N' adjacent conversion elements 54 from the M conversion elements 54 constituting the electroacoustic conversion unit 23, at the time of transmission in the pulse echo method. At the time of reception in the photoacoustic imaging method, the electronic switch 53 selects the N adjacent conversion elements 54 from the M conversion elements 54. At the time of reception in the pulse echo method, the electronic switch 53 selects the N' conversion elements 54. The electronic switch 53 then supplies the reception signals obtained by the N and N' conversion elements 54 to the preamplifiers 55.

The preamplifiers 55 amplify the small reception signals received by the N' conversion elements 54 that have been selected by the electronic switch 53. This ensures sufficient S/N.

The reception delay circuits 56 gives delay times to the acoustic reception signals or ultrasonic reception signals obtained from the N or N' (M>N', M>N) conversion elements 54 selected by the electronic switch 53. A convergent reception beam can therefore be generated by matching the phases of the acoustic waves or reception ultrasonic waves generating from a predetermined region.

The adder 57 combines the ultrasonic reception signals supplied from the N' channels or the acoustic reception signals supplied from the N channels. In either case, the adder 57 generates one reception signal. Namely, the adder 57 performs phased addition of the reception signals of the N' or N channels, which are generating from a predetermined depth. Performing this phased addition, the adder 57 sets a reception conversion point.

The rate signal generating unit 21 generates clock pulses for setting the timing of transmitting ultrasonic pulses with a predetermined repetition frequency. The repitation frequency depends on the depth of field of an image. It is 4 kHz to 8 kHz in this embodiment.

The scan control unit 24 includes a conversion-element selection control circuit 68 and beam focusing control circuit 67. The selection control circuit 68 supplies to the electronic switch 53 the position information about the N' conversion elements 54 that the electronic switch 53 selects at the time of transmission. The conversion-element selection control circuit 68 also supplies to the electronic switch 53 the information about the N or N' conversion elements 54 selected at the time of reception. The beam focusing control circuit 67 supplies delay time information, from which the N conversion elements 54 and N' conversion elements 54 will form a transmission convergence point and a reception convergence point, to the transmission delay circuit 51 and reception delay circuit 56.

The signal processing unit 25 includes a filter 66, logarithmic transformation unit 58, envelope detector 59, A/D converter 60, image data memory A 61, and image data memory B 62. The filter 66 removes unnecessary noise from an output from the adder 57 of the transmission/reception unit 22. The logarithmic transformation unit 58 logarithmically transforms the amplitude of the signal output from the filter 66, relatively enhancing this weak signal. Signals from the subject 7 generally have amplitude in a wide dynamic range of 80 dB or more. To display them on a general CRT monitor having a dynamic range of about 23 dB, amplitude compression must be carried out to enhance the weak signal.

The filter 66 can operate in two modes. In the first mode, it extracts the fundamental wave of a reception signal. In the second mode, it extracts harmonic components. The envelope detector 59 detects the envelope of a reception signal logarithmically transformed. The A/D converter 60 performs A/D conversion, converting the output signal from the envelope detector 59 into image data.

This image data includes data (hereinafter referred to as "photoacoustic image data") that the photoacoustic imaging method generates from a photoacoustic reception signal obtained when light is applied to the subject 7. The image data further includes the data (hereinafter referred to as "ultrasonic image data") that the normal pulse echo method generates from the ultrasonic reception signal, or reflected wave, obtained when a ultrasonic wave is transmitted to the subject 7. The image data memory A 61 is a storage circuit that stores the former photoacoustic image data. The image data memory B 62 is a storage circuit that stores the latter ultrasonic image data.

The display unit 6 includes a display image memory 63, converter 64, and CRT monitor 65. The display image memory 63 is a buffer memory that temporarily stores image data to be displayed on the CRT monitor 65. The photoacoustic image data stored in the image data memory A 61 and the ultrasonic image data stored in the image data memory B 62 are combined in the display image memory 63. The converter 64 performs D/A conversion and TV format conversion on the image data read from the display image memory 63. The CRT monitor 65 displays the output of the converter 64.

The operation unit 5 has a keyboard, trackball, mouse, and the like, all mounted on the operation panel. When operated, the unit 5 inputs necessary information such as subject information and imaging conditions for the apparatus.

The system control unit 4 has a CPU (not shown) and storage circuit (not shown). The unit 4 controls, for example, the optical transmission unit 1, image data generating unit 2, and display unit 6, in accordance with command signals supplied from the operation unit 5. The unit 4 controls the entire system, too. When operated, the operation unit 5 generates input command signals. The input command signals are stored into the CPU provided in the system control unit 4.

The irradiation unit 15 and electroacoustic conversion unit 23 are formed integral with each other, providing an applicator 70. The applicator 70 will be described, with reference to FIGS. 3A to 4. FIG. 3A explains a method of arraying the optical fibers 71 to form the waveguide unit 14, and the conversion elements 54 to form the electroacoustic conversion unit 23. M conversion elements 54-1 to 54-M, each having a length s, thickness t, and width a, are arranged in a line, at intervals d. The optical fibers 71 are laid in the gaps between the conversion elements 54, each at the middle of one conversion element 54 in the longitudinal direction. The optical fibers 71 are spaced from one another in the same direction the conversion elements 54 are arrayed.

FIG. 3B is a sectional view of the applicator 70, taken along line A—A in FIG. 3A. The applicator 70 may be brought into direct contact with the skin of the subject 7 to irradiate the subject with light and receive acoustic waves and ultrasonic waves from the subject 7. The applicator 70 incorporates optical fibers 71 for radiating light, and conversion elements 54 for receiving acoustic signals and transmitting/receiving ultrasonic waves. Electrodes 73-1 and 73-2 are mounted, respectively on the first surface (upper surface) and second surface (lower surface) of each conversion element 54. The electrodes 73-1 and 73-2 are provided to supply a driving signal and receive a reception signal. The electrode 73-1 is secured to a support 72. An acoustic matching layer 74 is formed on the other electrode 73-2 to accomplish efficient transmission/reception of ultrasonic waves. A protective film 75 covers the acoustic matching layer 7401. In FIG. 3A, the support 72, acoustic matching layer 74, and protective film 75 are not shown for the sake of simplicity.

Figure 4:
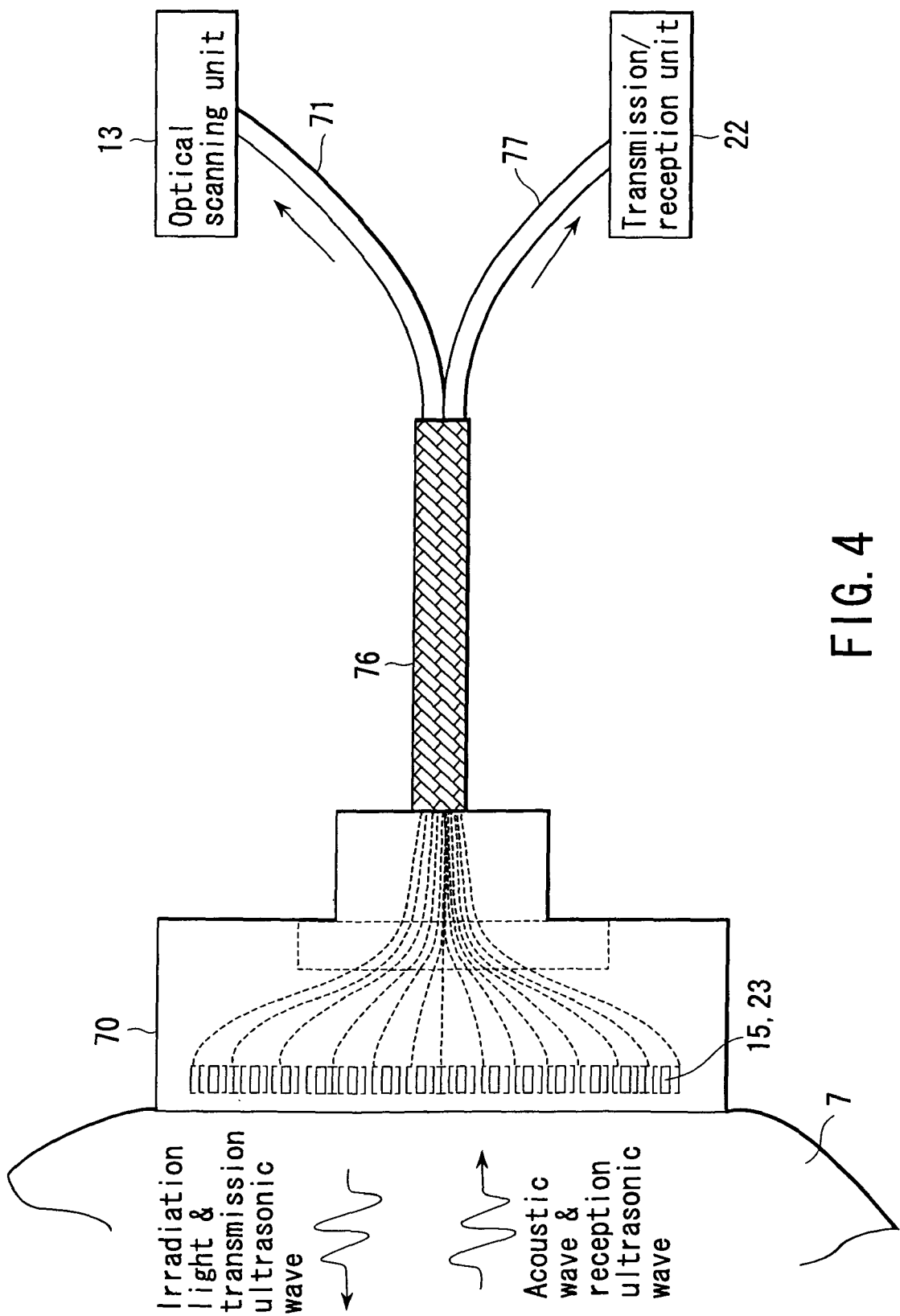
FIG. 4 is a diagram showing an outer appearance of the applicator according to the first embodiment of the invention.

FIG. 4 shows an outer appearance of the applicator 70. The electroacoustic conversion unit 23 and irradiation unit 15, which are arranged on the left surface of the applicator 70, are moved to contact the surface of the subject 7. The unit 15 irradiates the subject with irradiation light. The unit 23 receives acoustic waves and transmit/receive ultrasonic waves. The optical fibers 71 are connected at one end to the irradiation unit 15. The coaxial cables 77 are connected at one end to electrodes 73 of the conversion elements 54. The optical fibers 71 and coaxial cables 77 are bundled in a sheath 76. The optical fibers 71 are connected at the other end to the optical scanning unit 13. The coaxial cable 77s are connected at the other end to the transmission/reception unit 22 of the image data generating unit 2.

Figure 5:
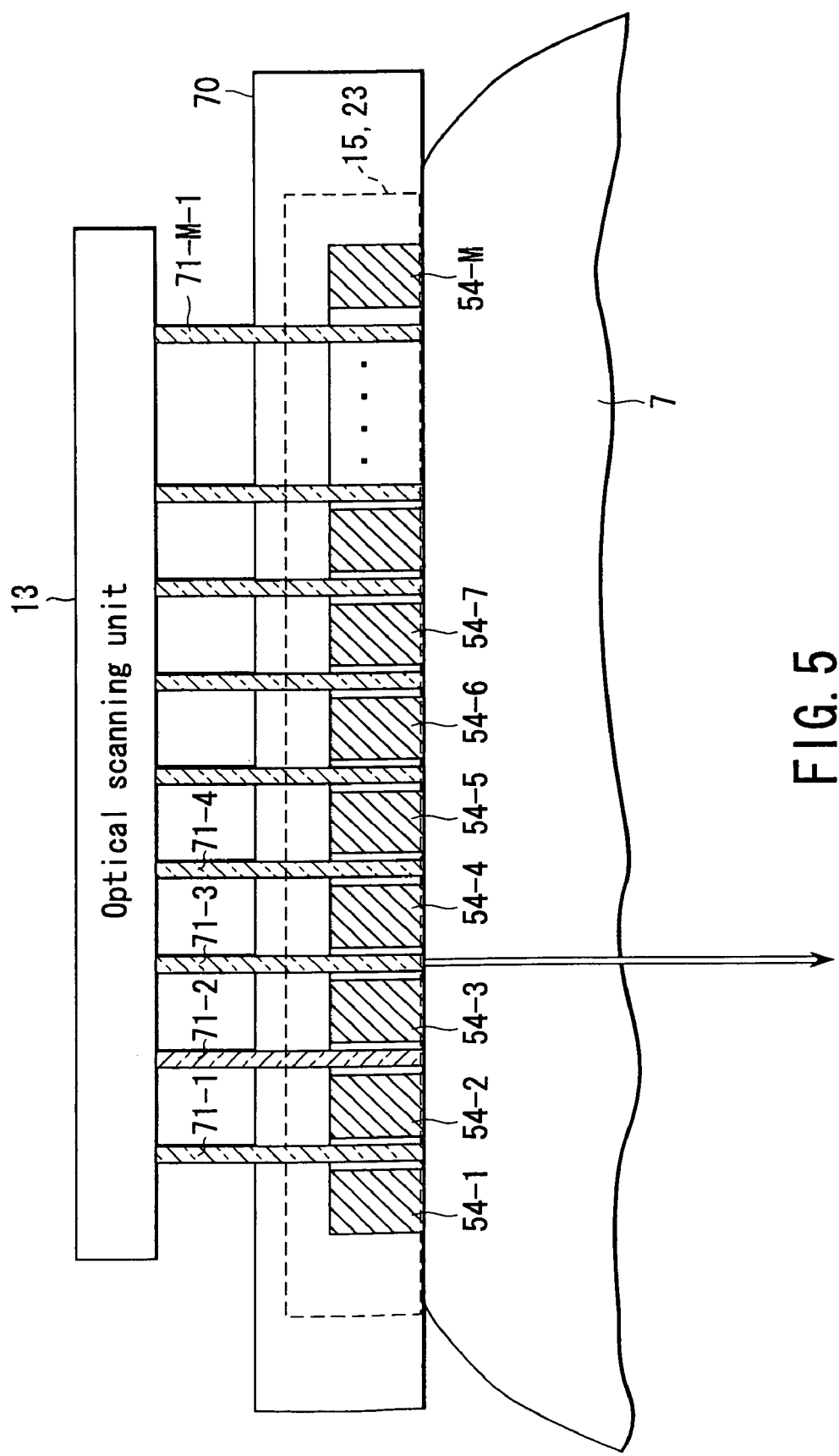
FIG. 5 is a diagram depicting an irradiation method using optical fibers, according to the first embodiment of the present invention.
Figure 6:
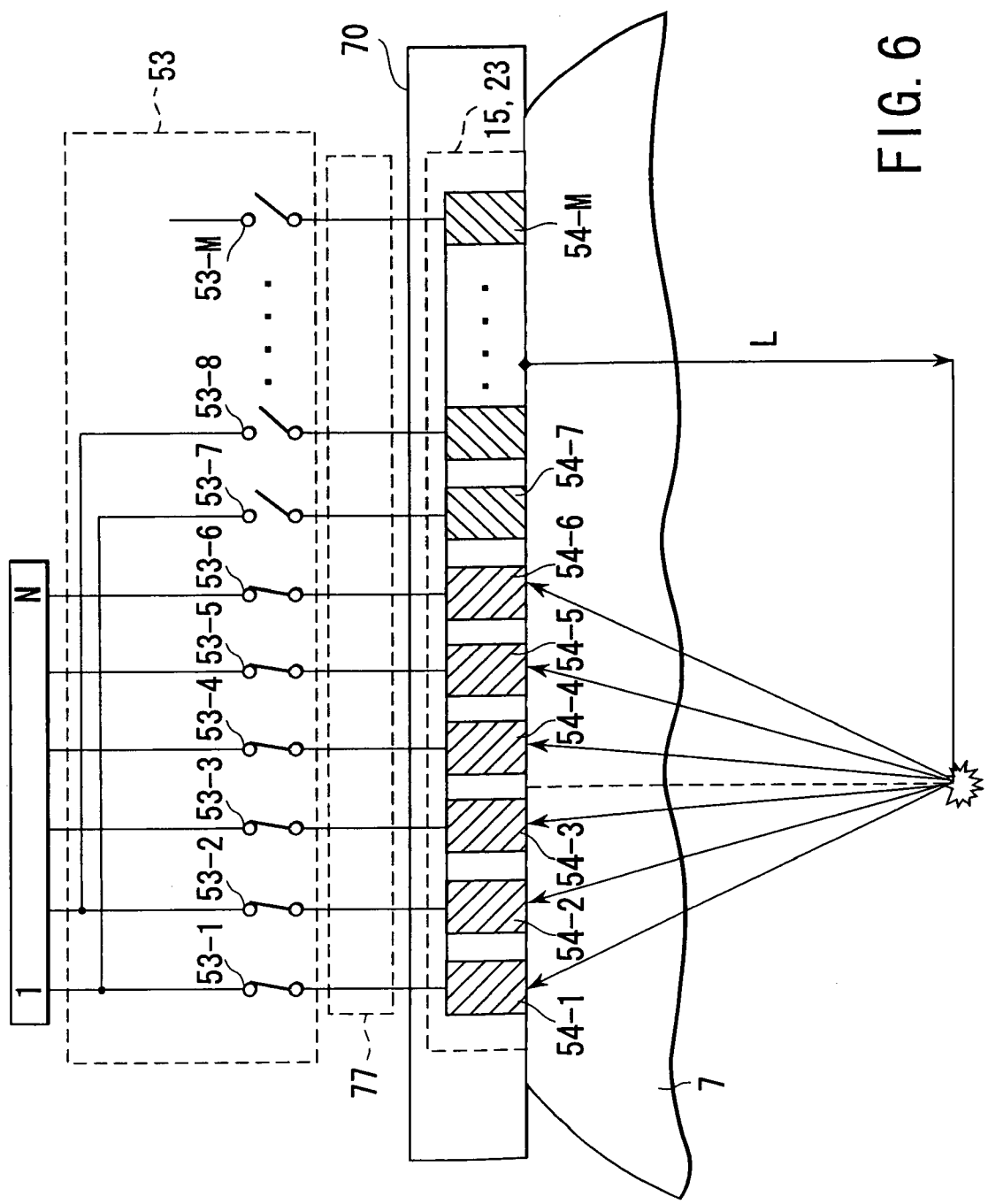
FIG. 6 is a diagram explaining a method of receiving acoustic waves, according to the first embodiment of the present invention.

How photoacoustic image data is generated in the first embodiment of the present invention will be described with reference to FIGS. 1 to 6. FIG. 5 explains a method of radiating irradiation light in the applicator 70. FIG. 6 shows a method of receiving acoustic waves in the applicator 70. In FIG. 6, the support 72, acoustic matching layer 74, and protective film 75 are not illustrated for simplicity.

The operator operates the operation unit 5 to set necessary imaging conditions for the photoacoustic imaging method and pulse echo method. The imaging conditions include various specifications of the applicator 70, in addition to a frame count, field depth, rate frequency, and type of the image display method. At the same time, the operator also sets conditions concerning a light source, such as the wavelength of light used for photoacoustic imaging. The imaging conditions thus set are stored into a storage circuit (not shown) that is incorporated in the system control unit 4.

When setting of the above imaging conditions is completed, the operator sets the applicator 70 at a predetermined position on the subject 7, and then inputs a command to the operating unit 5 to start acquisition of photoacoustic image data using photoacoustic imaging. Upon receipt of the command for staring acquisition of photoacoustic image data, the system control unit 4 reads the conditions set for the light source, from the internal storage circuit. In accordance with the conditions, the light source unit 11 selects, for example, an Nd·YAG laser, which emits monochromatic light having a wavelength of 1,000 nm. The monochromatic light is applied to the optical scanning unit 13 via the optical multiplexing unit 12. The optical scanning unit 13 selects, for example, the optical fiber 71-3 from the optical fibers 71 (71-1 to 71-M-1) arrayed as shown in FIG. 5. The monochromatic light is applied to the optical fiber 71-3 selected. The fiber 71-3 guides the light to the irradiation unit 15 of the applicator 70. The applicator 70 irradiates the subject 7 with light from the distal end portion of the irradiation unit 15. In this case, the monochromatic light is applied to the subject 7, almost perpendicular to that surface part of the subject 7 which contacts the applicator 70, as indicated by the arrow in FIG. 5.

The hemoglobin in the blood of the subject 7 absorbs the energy of the monochromatic light and then are heated. The thermal expansion of the heated hemoglobin induces a local pressure change. Then, the local pressure change generates an acoustic wave. The acoustic wave is a pulse wave that has a broadband spectrum component of 100 kHz to 2 MHz.

In the photoacoustic imaging method, the wavelength of light to be applied to the subject is determined from the substance that should be measured, and the substance can be quantified from the magnitude of acoustic waves obtained by irradiating the subject with light having the wavelength determined. Thus, the amount of hemoglobin in an internal region of the subject 7 can be measured by irradiating the region with the monochromatic light emitted from the above Nd·YAG laser and having a wavelength of 1,000 nm.

After the irradiation of the subject 7 with light, acoustic waves are received. For example, with respect to a blood vessel area in a region a distance L away from the subject contact surface of the applicator 70 shown in FIG. 6, the system control unit 4 supplies selection information for the conversion elements 54 in the scanning information stored in advance in the storage circuit to the conversion-element selection control circuit 68 of the scan control unit 24, and also supplies delay time information concerning focal length setting at the time of reception to the beam focusing control circuit 67 of the scan control unit 24.

The electronic switch 53 receives a control signal from the conversion-element selection control circuit 68. In accordance with the control signal the switch 53 selects N (N=6) conversion elements 54-1 to 54-6 from the M conversion elements 54-1 to 54-M of the applicator 70. In accordance with a control signal from the beam focusing control circuit 67, the reception delay circuit 56 delays the reception signals obtained by the conversion elements 54, to set the reception focal length to L. That is, the selection control circuit 68 turns on electronic switches 53-1 to 53-N (N=6) in accordance with the selection information that is supplied for the conversion elements 54 from the system control unit 4. The conversion elements 54-1 to 54-6, centered on the optical fiber 71-3 selected/used for the radiation of light, are thereby selected to receive the acoustic waves generating from inside the subject 7. The conversion elements 54-1 to 54-6 convert the acoustic waves into electrical signals. These signals are supplied to the preamplifier 55 via the electronic switch 53. The preamplifier 55 amplifies the signals to a predetermined amplitude. The signals amplified are input to the reception delay circuit 56.

Of the reception delay circuits 56 constituted by N channels, the nth reception delay circuit 56 delays the reception signal supplied from the conversion element 54-$n$ by delay time $\tau(n)$, given by:

$$\tau(n) = d^2(N'-1)^2 - (2n - N - 1)^2 / 8CF_0 \quad (1)$$

where d is the interval of the conversion elements 54, C is the acoustic wave propagation speed (about 1,500 m/sec) in the subject 7, Fo is the reception focal length. If Fo=L, the delay times is imparted to the signals generated by the conversion elements 54-1 to 54-6. The adder 57 adds the signals delayed. The signals are thereby combined, while matching the phases of the acoustic waves generated at the distance L.

In this embodiment, the period between the time the subject 7 is irradiated with light and the time the conversion element 54 receives the acoustic wave is proportional to the distance L. Therefore, what is called dynamic convergence method can be used, which increases the reception focal length Fo given by equation (1) at the time of receiving acoustic waves. The acoustic waves generated by irradiation using the optical fiber 71-3 can be received in a converged state. Photoacoustic image data of high sensitivity and high spatial resolution can be generated from these reception signals.

The filter 66 of the signal processing unit 25 removes noise components from the signals generated by the conversion elements 54-1 to 54-6 and then combined by the adder 57. The logarithmic transformation unit 58 performs amplitude compression on the signal output from the unit 25. The envelope detector 59 detects the amplituide-compressed signal. The A/D converter 60 converts the signal detected by the detector 59, into a digital signal. The digital signal is stored, as photoacoustic image data, into the image data memory A 61.

Upon completion of the first photoacoustic imaging scan, the second scan is performed by using the optical fiber 71-4. The optical scanning unit 13 selects the optical fiber 71-4 from the optical fibers 71 (71-7 to 71-M-1), in accordance with a control signal supplied from the system control unit 4. The irradiation unit 15 of the applicator 70 irradiates the subject 7 with the monochromatic light applied from the light source unit 11 through the optical fiber 71-4.

To process the new acoustic waves generating from inside the subject 7 irradiated with the light applied through the optical fiber 71-4, the conversion-element selection control circuit 68 turns on the electronic switches 53-2 to 53-7 in accordance with the selection information for the conversion elements 54. Note that this information has been supplied from the system control unit 4. The control circuit 68 selects the conversion elements 54-2 to 54-7 centered on the optical fiber 71-4, which are selected and used for reception at the time of irradiating the subject 7. As in the first scan, the electronic switches 53-2 to 53-6 connect the conversion elements 54-2 to 54-6 are connected to preamplifiers 55-2 to 55-6 and reception delay circuits 56-2 to 56-6. The electronic switch 53-7 connects the conversion element 54-7 to the preamplifier 55-1 and reception delay circuit 56-1.

"#1" to "#5" show the reception delay circuits 56-2 to 56-6 to which reception signals from the conversion elements 54-2 to 54-6 are supplied, and "#6" shows the reception delay circuit 56-1 to which a reception signal from the conversion element 54-7 is supplied. Then, the reception signals supplied from the conversion elements 54 to the #n reception delay circuits 56 are delayed by the delay time of the equation (1). The adder 57 adds or combines the signals thus delayed. As in the first scan, the dynamic convergence method can be used in this scan, to receive, at all times, the acoustic waves generated inside the subject 7 in a converged state, regardless of the depth of the irradiated region. The signals from the conversion elements 54-2 to 54-7 and combined by the adder 57 are subjected to noise removal, amplitude compression, and envelope detection in the filter 66, logarithmic transformation unit 58, and envelope detector 59. The A/D converter 60 converts the output signal output of the detector 59 into a digital signal, which is stored into the image data memory A 61.

Subsequently, the system control unit 4 causes the optical scanning unit 13 to select the optical fibers 71-5, 71-6, . . . , 71-M-3 in the same manner as described above. Using the fibers selected, light is applied to the subject 7. At this time, the system control unit 4 causes the electronic switch 53 to select the conversion elements 54-3 to 54-8, 54-4 to 54-9, and 54-M-5 to 54-M. The conversion elements, thus selected, receive the newly generated acoustic waves. The reception signals from the six channels are sequentially stored into the image data memory A 61 via the preamplifiers 55, reception delay circuits 56, filter 66, logarithmic transformation unit 58, envelope detector 59, and A/D converter 60. Thus, one-frame image data is completely acquired.

When the photoacoustic image data is acquired by the photoacoustic imaging method finishes acquiring as described above, the pulse echo method is started to acquire ultrasonic image data. That is, upon confirming that the photoacoustic data has been acquired, the operator operates the operation unit 5, inputting a command for starting the pulse echo method to acquire ultrasonic image data. The ultrasonic image data acquired by the pulse echo method is displayed, together with the photoacoustic image data.

The system control unit 4 may supply an instruction signal for the first scan to be performed by the pulse echo method, to the beam focusing control circuit 67 of the scan control unit 24. Upon receipt of the instruction signal, the beam focusing control circuit 67 sends data for setting the convergence points of transmission ultrasonic waves and reception ultrasonic waves, to the transmission delay circuit 51 and reception delay circuit 56. The delay circuits 51 and 56 set delay times in accordance with the data. The conversion-element selection control circuit 68 of the scan control unit 24 supplies data regarding the conversion elements 54 of the electroacoustic conversion unit 23 selected and used in the first scan to the electronic switch 53, and turns on predetermined channels.

When these settings are performed, the rate signal generating unit 21 generates a pulse for determining the transmission timing of the first ultrasonic pulse. This pulse is supplied to the transmission delay circuits 51 constituted by N' channels. The delay circuits 51 delays the pulse by time τf for determining the convergence distance of transmission ultrasonic waves. The pulse delayed is supplied to the pulser 52. In this case, the delay time τf(n) in the n'th (n'=1 to N') delay circuit is set as follows:

$$\tau f(n')=d^2\{(N'-1)^2-(2n'-N'-1)^2\}/8CF_0 \quad (2)$$

where d is the interval between the conversion elements 54, C is the acoustic wave propagation speed in the subject 7, and Fo is the transmission convergence point.

The output from the rate signal generating unit 21, which has been delayed by the transmission delay time of equation (2), is supplied to the pulsers 52, driving the conversion elements 54. The conversion elements generate driving pulses, which will be used to irradiate the subject 7 with ultrasonic waves. Outputs of the pulsers 52, i.e., driving signals for the conversion elements 54, are supplied via the electronic switch 53 to the N' conversion elements 54-1 to 54-N' of the M arrayed conversion elements 54. The elements 54-1 to 54-N' generate transmission ultrasonic waves. The subject 7 is irradiated with the transmission ultrasonic waves.

In the subject 7, some of the ultrasonic waves are reflected by the interface between the organs, or the different tissues, or by the acoustic scatters in the living body tissue. The conversion elements 54 receive the waves reflected, as reception ultrasonic waves, and convert them into an electrical signal. The electronic switch 53 selects the ultrasonic wave reception signals obtained by the conversion elements 54-1 to 54-N. These N'-channel reception signals are sent to the reception delay circuits 56 via the preamplifiers 55. The signals are delayed by delay times and then supplied to the adder 57. The adder 57 adds or combines the N'-channel ultrasonic reception signals, generating a signal. This signal is subjected to noise removal, logarithmic compression in the filter 66, logarithmic transformation unit 58. It is then subjected to envelope detection in the envelope detector 59.

The signal, which is an analog signal, is converted to digital image data. In the image data, thus obtained in the first scan, is stored into the image data memory B 62. At the time of reception, the dynamic convergence method is preferably used. This method is the same as the photoacoustic imaging method described above, and will not be described in detail.

The same procedure as performed in the first scan is repeated, carried out the second and subsequent scans. In the second scan, the electronic switch 53 selects the conversion elements 54-2 to 54-N'+1. In the third scan, the electronic switch 53 selects the conversion elements 54-3 to 54-N'+2. Ultrasonic waves are then transmitted and received. This operation is repeated until the conversion elements 54-M-N+1 to 54-M are selected and driven. The transmission delay circuits 51 converge transmission ultrasonic beams. The reception delay circuits 56 converge reception ultrasonic beams. The method of setting delay times will not be described in detail, because it is almost identical to the method employed in the photoacoustic imaging method.

Thereafter, the one-frame image data obtained by the pulse echo method is stored into the image data memory B 62 of the signal processing unit 25. After the photoacoustic image data and ultrasonic image data are completely acquired, the system control unit 4 reads both image data items from the image data memory A 61 and image data memory B 62. The image data items are combined in the display image memory 63 and temporarily stored therein. The combined image data is supplied to the converter 64. The converter 64 performs D/A conversion and TV format conversion on the combined image data. The resultant image data is displayed on the CRT monitor 65.

Photoacoustic image data and ultrasonic image data are repeatedly acquired in this manner. They are combined and displayed on the CRT monitor 65. Thus, the operator can observe the combined image in real time.

The photoacoustic image data and ultrasonic image data are thus combined in the display image memory 63. The CRT monitor 65 displays these image data items, imposing one on the other. This makes it easy for the operator to identify the acoustic wave source from the photoacoustic image. It is desired that the ultrasonic image and photoacoustic image be displayed in different colors to enable the operator to distinguish one image from the other. For example, the ultrasonic image may be displayed monochromic, and the photoacoustic image may be displayed in red.

In the first embodiment, a photoacoustic image and an ultrasonic image can be acquired by the conversion elements 54 of the same type. Therefore, the images can be superimposed and displayed with high precision. To generate a photoacoustic image, in particular, the acoustic reception signals that many conversion elements 54 generate are added, with their phases matched by virtue of what is called "phased addition scheme". Therefore, the acoustic wave source can be accurately identified even if, for example, light radiated on the subject 7 is scattered and diffused.

The above description of the first embodiment is based on the assumption that six conversion elements are used to acquire acoustic reception signals for photoacoustic imaging. More conversion elements can be used, nonetheless. The number of conversion elements used for transmission and the number of conversion elements used for reception may be different from N'.

As indicated above, ultrasonic image data is acquired after photoacoustic image data is acquired in the first embodiment. The order of acquisition of the image data items may be reversed. In addition, photoacoustic image data and ultrasonic image data corresponding to a plurality of frames may be acquired. In this case, they may be temporarily stored in the image data memory A 61 and image data memory B 62, respectively. Desired image data items can be read from the image data memories A 61 and B 62 and be combined in the display image memory 63.

To acquire photoacoustic image data, light beams having different wavelengths may be used determine the content of one substance. How the content of, for example, hemoglobin is measured will be described. As mentioned above, hemoglobin in the living body absorbs light in the range of 600 nm to 1,000 nm. Deoxyhemoglobin absorbs more light having a wavelength near 600 nm than oxyhemoglobin does. On the other hand, the amount of light absorbed by oxyhemoglobin absorbs more light having a wavelength near 1,000 nm than deoxyhemoglobin does. This difference in absorption property, oxyhemoglobin and deoxyhemoglobin in the subject may be independently quantified, or the total amount of both types of hemoglobin can be determined. Light emitted from a 1,000 nm Nd:YAG laser and light emitted from a 633 nm He—Ne gas laser may be applied to the subject, thereby to measure the content of oxyhemoglobin and that of deoxyhemoglobin, respectively. In this case, a photoacoustic image and an ultrasonic image may be displayed side by side, or one superimposed on the other.

The contents of a substance other than hemoglobin, for example, cholesterol or glucose, may be measured in the same region in the subject 7 by using monochromatic light having an optimal wavelength and by performing the same procedure as described above. The content measured and the content of hemoglobin, measured beforehand, may be displayed in different colors, distinguishing one from the other. In this case, too, the display method is not specifically limited. The photoacoustic image and ultrasonic image may be displayed, side by side or one superimposed on the other.

Second Embodiment:

The second embodiment of the present invention will be described with reference to FIGS. 7A to 7C. In the second embodiment, the harmonic imaging method acquires ultrasonic image data. The method of acquiring photoacoustic image data and the method of transmitting ultrasonic waves in the pulse echo method, both performed in this embodiment, are identical to those used in the first embodiment. Therefore, they will not be described.

In the photoacoustic imaging method, the frequency spectrum of an acoustic wave ranges from 200 kHz to 2 MHz, with 1 MHz being the center frequency. The conversion elements 54 of the electroacoustic conversion unit 23 must have properties that correspond to such frequency components. The center frequency is lower than the center frequency (for example, fo: 3.5 MHz) that is applied in standard pulse echo methods.

In the first embodiment, the same conversion elements 54 acquire both the photoacoustic image data and the ultrasonic image data. Thus, the ultrasonic image obtained by the conventional pulse echo method inevitably deteriorates in spatial resolution.

It will be described how ultrasonic image data should be acquired by the harmonic imaging method in order to solve this problem. The harmonic imaging method effectively utilizes the ultrasonic nonlinear phenomenon that occurs in the tissue of the subject 7. When, for example, an ultrasonic pulse with a center frequency fo is applied to a subject 7, a second harmonic component (2fo) is generated due to the nonlinear phenomenon in the tissue to be examined. A conversion element 54 receives the harmonic component, together with a fundamental wave component. The generation of this harmonic component depends on the tissue properties of the subject 7 and also on the propagation distance to a reflecting region or ultrasonic intensity at the reflecting region.

In the acquisition of ultrasonic image data, some of the transmission ultrasonic waves applied to the subject 7 are reflected by the interface between organs of the subject 7, which differ in acoustic impedance or by a tissue. From the ultrasonic waves reflected, ultrasonic pulses are generated due to the nonlinear properties of the tissue. The ultrasonic pulses have a center frequency 2fo. Therefore, the reception ultrasonic wave that reflected by the tissue in the subject 7 reflects and the conversion element 54 receives contains both an ultrasonic pulse (fundamental wave component) having the center frequency fo at the time of transmission and an ultrasonic pulse (harmonic component) having the center frequency 2fo.

Figure 7A:
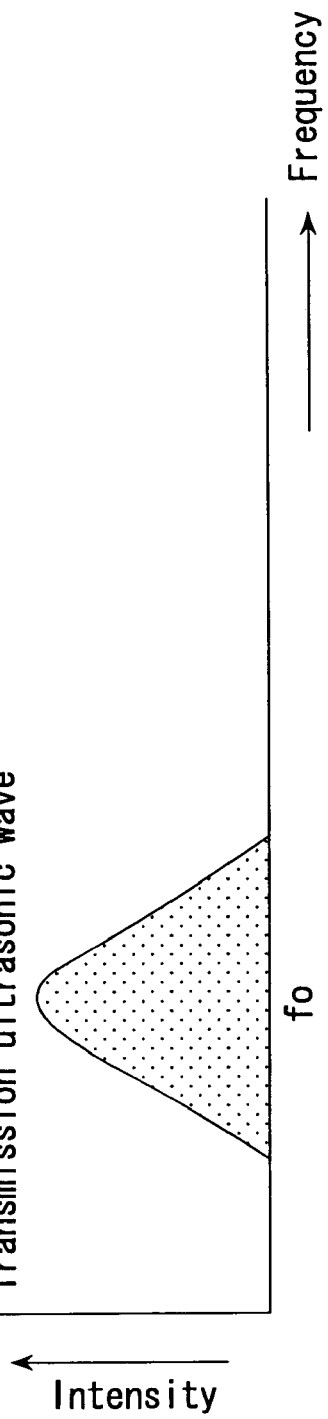
FIGS. 7A to 7C are graphs showing the frequency spectrum of a received ultrasonic wave according to the second embodiment of the present invention.
Figure 7B:
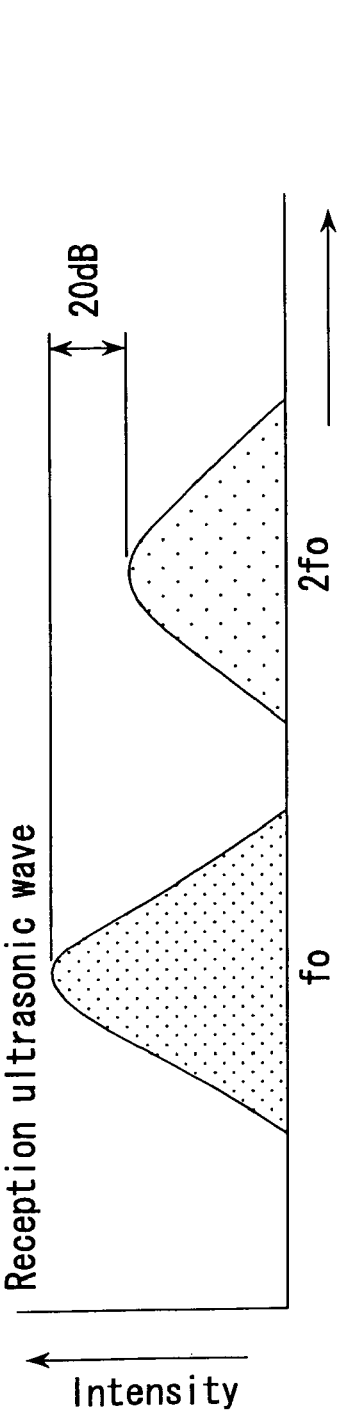
Figure 7C:
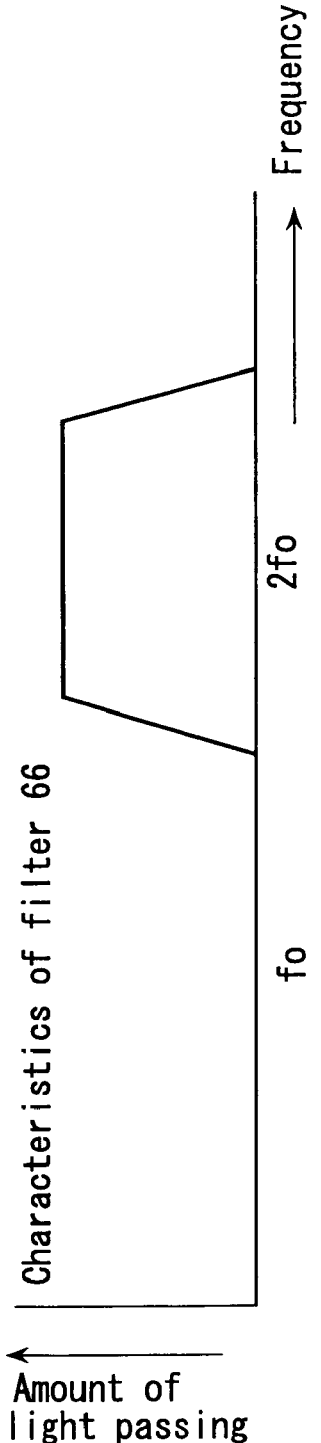

FIG. 7 shows a frequency spectrum of the ultrasonic wave assumes at this time. FIG. 7A shows the frequency spectrum of a transmission ultrasonic wave to be transmitted to the subject 7. Note that this frequency spectrum is distributed on the center frequency fo. In contrast, the frequency spectrum of the reception ultrasonic wave from the subject 7 shown in FIG. 7B is made up of a fundamental wave component and a harmonic component. The fundamental wave component is distributed, centered on fo, and the harmonic component is distributed, centered on 2fo. Generally, a harmonic component is smaller than a fundamental wave component by about 20 dB. As is known, the harmonic component is generated since the speed with which an ultrasonic pulse propagates in the subject tissue depends on the sound pressure of an ultrasonic wave, and this distorts the waveform of a reception signal.

The conversion element 54 receives a reception ultrasonic wave from the subject 7 and converts it into an electrical signal (ultrasonic reception signal). The ultrasonic reception signal is sent to the filter 66 of a signal processing unit 25 through a transmission/reception unit 22. The filter 66 has a bandpass characteristic centered on 2fo as shown in FIG. 7C and a bandpass characteristic (not shown) centered on fo. In the harmonic imaging method, the filter 66 extracts a second harmonic component. The output of the filter 66 is stored into an image data memory B 62 via a logarithmic transformation unit 58, envelope detector 59, and A/D converter 60. In the photoacoustic imaging method, too, the filter 66 extracts a fundamental wave component, and the output of the filter 66 is stored into an image data memory B 62 via the logarithmic transformation unit 58, envelope detector 59, and A/D converter 60.

The system control unit 4 reads the ultrasonic image data stored in the image data memory B 62 and the photoacoustic image data stored in an image data memory A 61. The ultrasonic image data and the photoacoustic image data are combined in a display image memory 63, providing a combined image data. The combined image data is supplied to a CRT monitor 65 via a converter 64. The CRT 65 display the image represented by the combined image data.

According to the second embodiment, ultrasonic image data is generated from ultrasonic waves having a frequency twice as high as the ultrasonic waves used in the first embodiment. Therefore, even if the conversion elements 54 is used to acquire both displayed, to provide an apparatus with excellent operability.

In the second embodiment described above, the harmonic imaging method is performed, in which second harmonic components are used. Nonetheless, a third or higher-order harmonic component may be used to generate ultrasonic image data.

Third Embodiment:

The third embodiment of this invention is a simplified reception method that may be employed in photoacoustic imaging. This reception method will be described with reference to FIG. 8. The method of acquiring ultrasonic image data and the method of irradiating a subject, both performed in the photoacoustic imaging method in this embodiment, are identical to those employed in the first embodiment. They will not be described.

Figure 8:
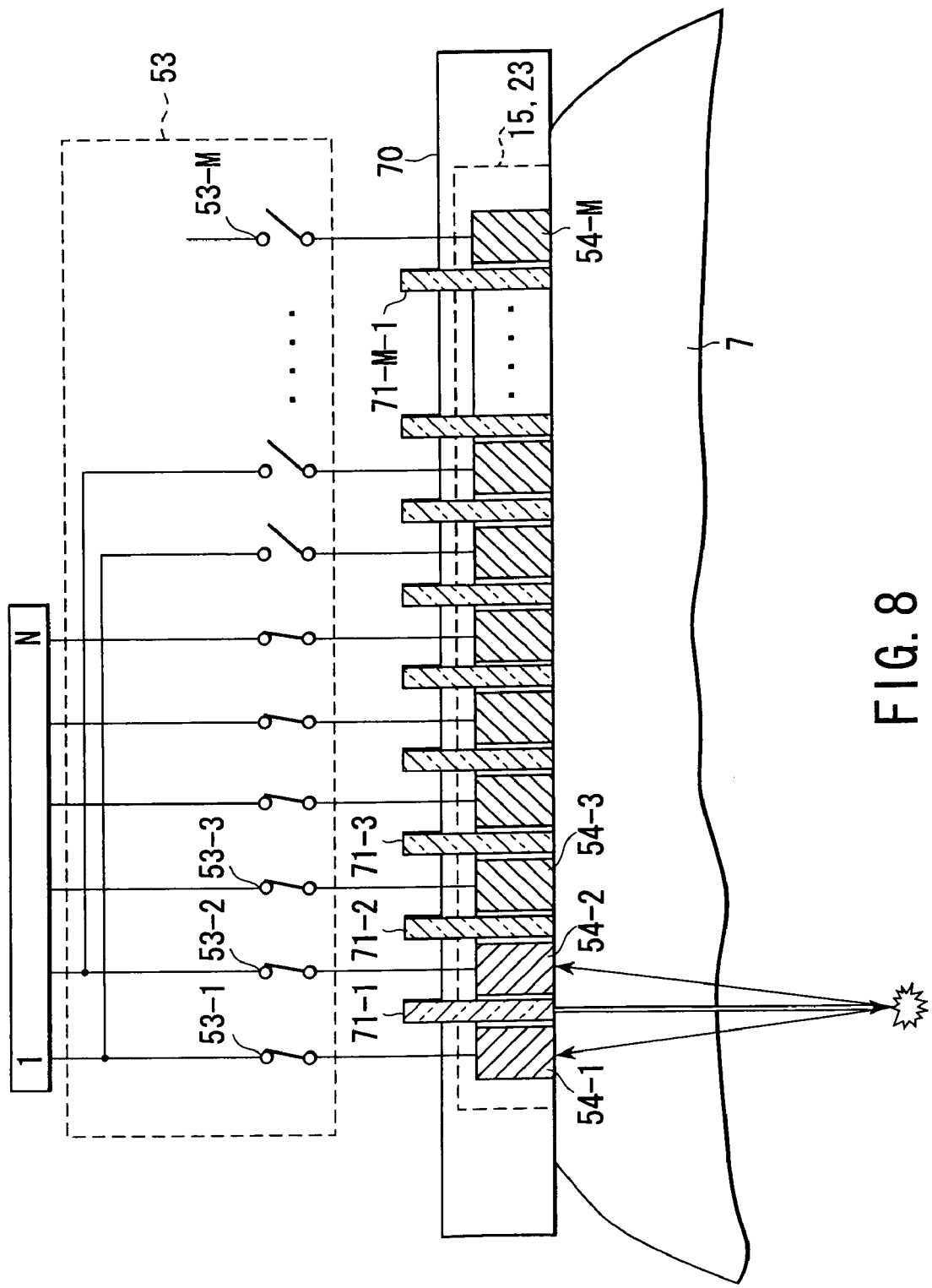
FIG. 8 is a diagram showing the position where irradiation light is applied and the positions where acoustic waves are received in the third embodiment of the invention.

FIG. 8 shows the position where irradiation light is applied and the positions where acoustic waves are applied, in the third embodiment. The subject 7 is irradiated with light applied through an optical fiber 71-1 as shown in FIG. 8. The light travels straight, while maintaining its small diameter. That is, it exhibits good directivity. Therefore, a photoacoustic image can be generated without performing phased addition processing at the time of reception of acoustic waves.

In the first scan in photoacoustic imaging, the subject 7 is irradiated with light emitted from the optical fiber 71-1. The hemoglobin in the blood flowing in the subject 7 absorbs the energy of the light and produces acoustic waves. Upon receipt of the acoustic waves, a system control unit 4 supplies information for selecting conversion elements 54, to a conversion-element selection control circuit 68 of a scan control unit 24. The information is included in the scan information that has been stored in the storage circuit of the system control unit 4.

The conversion-element selection control circuit 68 receives the information for selecting the conversion elements 54 from the system control unit 4. In accordance with the information, the circuit 68 closes electronic switches 53-1 and 53-2, selecting conversion elements 54-1 and 54-2 that are located on the sides of the optical fiber 71-1 selected at the time of irradiation with light. The elements 54-1 and 54-2 selected function as conversion elements for reception. The conversion elements 54-1 to 54-6 convert the acoustic waves generated inside the subject 7, into electrical signals. The electrical signals are supplied via an electronic switch 53 to preamplifiers 55. The preamplifier 55 amplifies the signals to predetermined amplitudes. The signals output from the preamplifier 55 are input to reception delay circuits 56. The circuits 56 are used to acquire ultrasonic image data to be simultaneously displayed. They are not used to acquire the photoacoustic image data. That is, the signals obtained by the conversion elements 54-1 and 54-2 pass through the reception delay circuits 56, without being processed. An adder 57 combines the signals.

The signal processing unit 25 has a filter 66. The filter 66 removes noise components from the acoustic reception signals supplied from the conversion elements 54-1 and 54-2 and combined by the adder 57. The output signal of the filter 66 is supplied to a logarithmic transformation unit 58. The unit 58 performs amplitude compression on the signal, which is supplied to an envelope detector 59. The detector 59 detects the signal subjected to the amplitude compression. An A/D converter 60 converts this signal into a digital signal. The digital signal is stored into an image data memory A 61 for photoacoustic image data.

In the second scan, the subject 7 is irradiated with light applied from a optical fiber 71-2. As a result, acoustic waves generate from the subject 7. The conversion elements 54-2 and 54-3 receive the acoustic waves and generate acoustic image data from the acoustic waves. The acoustic image data is stored into the image data memory A 61, as in the first scan. This sequence of operations is repeated until image data is acquired by using an optical fiber 71-M-1 and conversion elements 54-M-1 and 54-M. The image data acquired represents a one-frame photoacoustic image. It is stored into the image data memory A 61.

The photoacoustic image data stored in the image data memory A 61 and the ultrasonic image data acquired by the succeeding pulse echo method and stored in an image data memory B 62 are combined in a display image memory 63. The combined image data is supplied via a converter 64 to a CRT monitor 65. The CRT monitor 65 displays the image represented by the combined image data.

In the third embodiment, the number of vibrators used for reception can be greatly reduced. Thus, optical fibers 71 provided at end portions can be effectively used. This makes it possible to obtain a wide image width (viewing width).

In the third embodiment, two conversion elements are used to receive acoustic waves. The number of conversion elements used is not limited to two, nevertheless.

Fourth Embodiment:

In the first to third embodiments described above, the optical fibers 71 are laid in the gaps between the conversion elements 54 as shown in FIG. 3, if the fibers 71 and conversion elements 54 are arrayed in the same direction. In this case, acoustic coupling occurs between the respective adjacent conversion elements 54, because the optical fibers 71 are inserted in their gaps. Consequently, each conversion element fails to function as so efficient an independent element as is desired. Hence, the acoustic coupling may degrade both the photoacoustic image and the ultrasonic image in terms of quality.

In the fourth embodiment, optical fibers 71 are arranged without degrading the performance of conversion elements 54 provided in integrating the optical fibers 71 or the performance of the conversion elements 54 provided in an applicator 70. A method for arranging fibers 71 will be described with reference to FIGS. 9 to 11.

Figure 9:
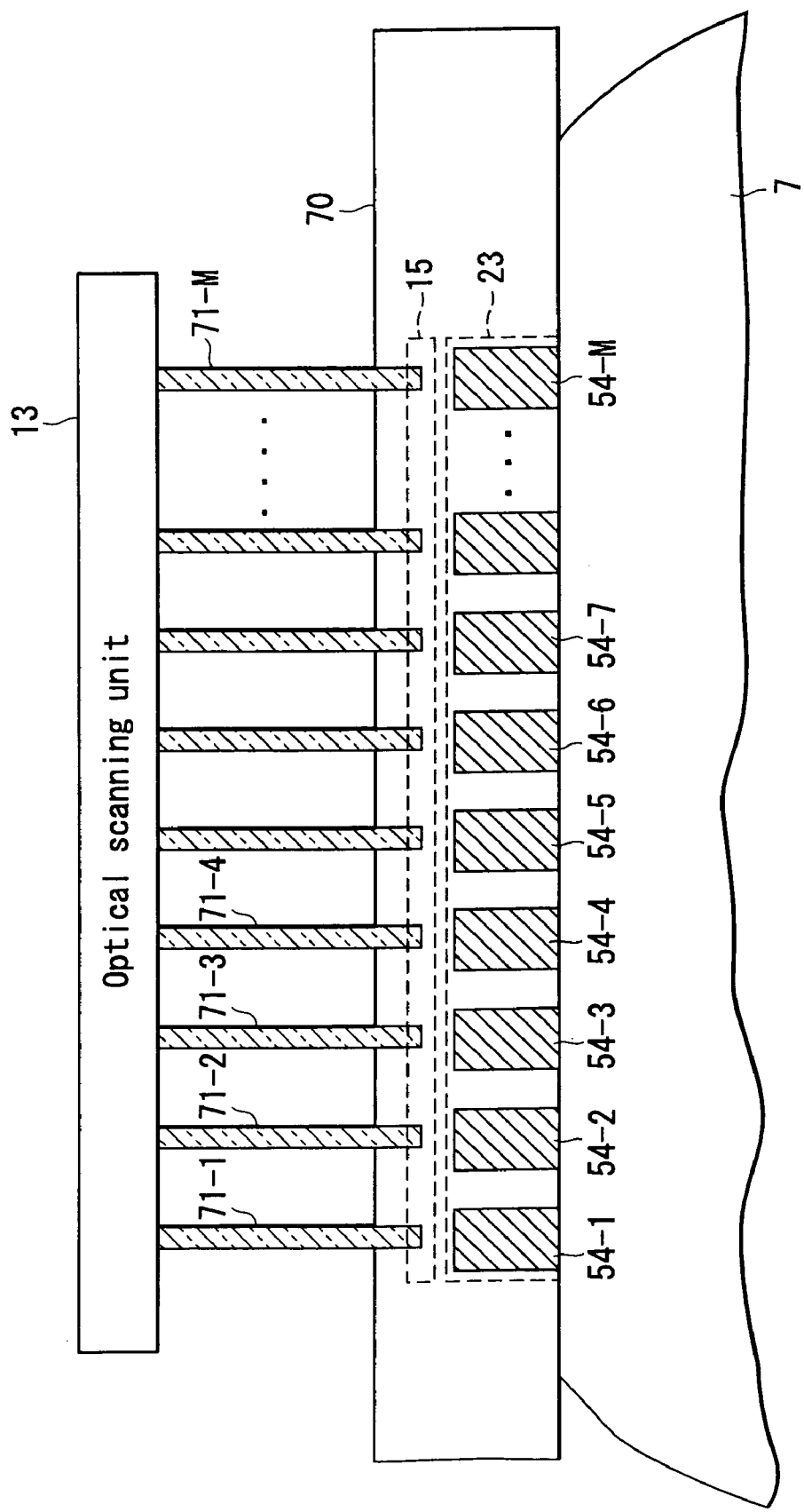
FIG. 9 is a diagram illustrating an applicator according to the fourth embodiment of the present invention.

FIG. 9 shows the arrangement of the applicator 70 used in this embodiment. In this applicator 70, an irradiation unit 15 serving as the output terminal of each optical fiber 71 and an electroacoustic conversion unit 23 having conversion elements 54 are integrated as in the applicator 70 that is used in the first to third embodiments. However, the applicator 70 is designed to irradiate a subject 7 with the light emitted from the irradiation unit 15 and transmitted through the electroacoustic conversion unit 23. That is, the electroacoustic conversion unit 23 is made of material that is transparent to the light.

Figure 10:
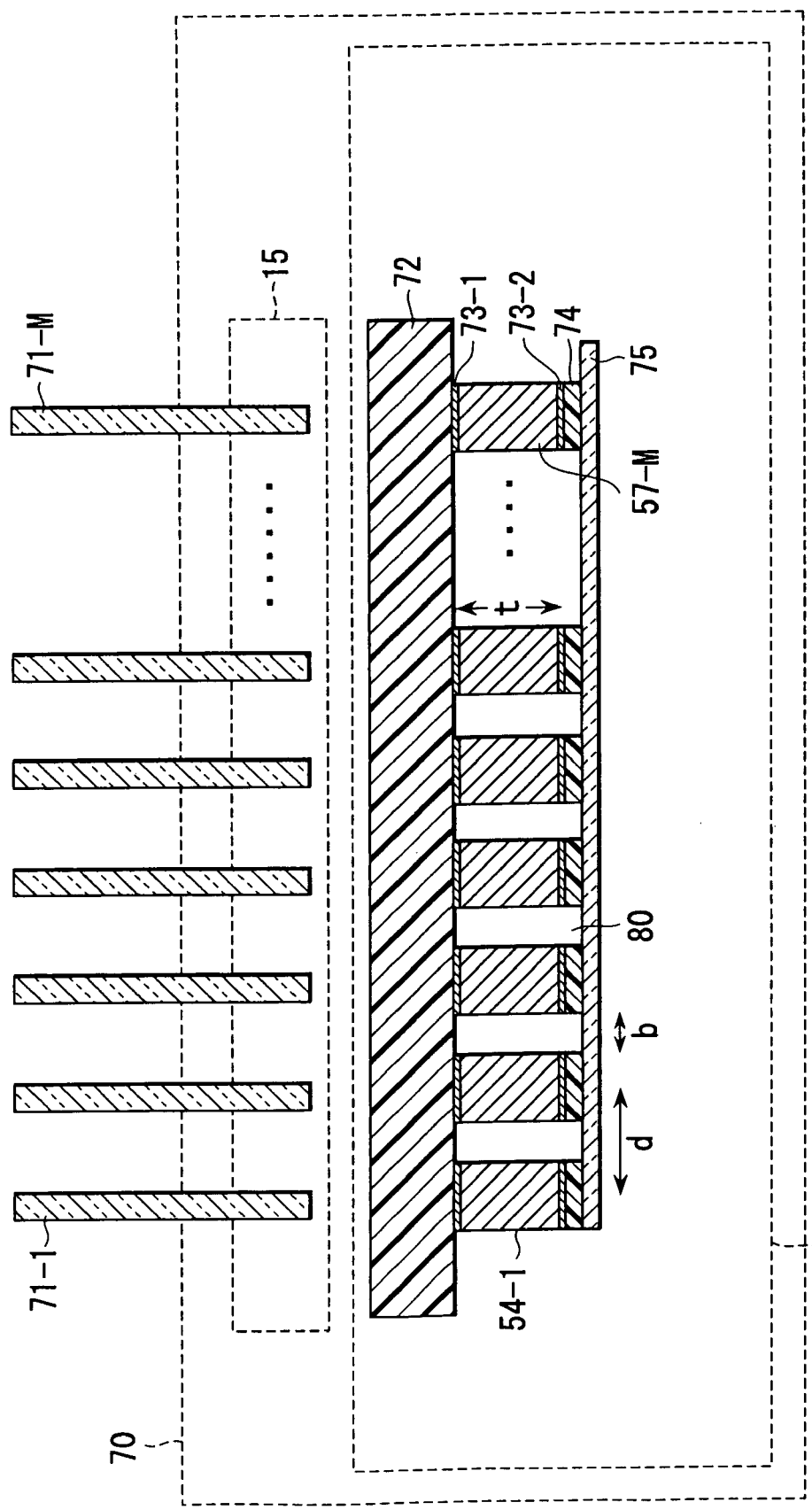
FIG. 10 is a diagram depicting an electroacoustic conversion unit according to the fourth embodiment of this invention.

Each material forming this electroacoustic conversion unit 23 will be described with reference to FIG. 10. FIG. 10 shows the applicator 70 used in the fourth embodiment. The conversion elements 54 of the electroacoustic conversion unit 23 have been formed as follows. A PZNT single-crystal wafer made of transparent piezoelectric material is polished to a predetermined thickness t. The resultant single-crystal plate is cut by a dicing saw into pieces that are arrayed with a pitch d. The gap between any two adjacent pieces, having a width b, is filled with an optically transparent resin 80. The resin 80 is cured.

Electrodes 73-1 are formed by sputtering on the first surfaces of the single-crystal elements arrayed one-dimensionally. Electrodes 73-2 are formed by sputtering on the second surfaces of the elements by sputtering.

An acoustic matching layer 74 and protective film 75 are stacked, one upon another, on each surface on which the electrode 73-2 is mounted. Note that both the acoustic matching layer 74 and the protective film 75 are made of optically transparent resin. An electrode 73 is made of, for example, transparent, conductive material such as ITO (indium-tin-oxide) or $In_2O_3$ (Sn), used for a liquid crystal display, plasma display, and the like. Thus, transparent, conductive material is used for the electrodes 73, and optically transparent resin is used for the acoustic matching layer 74 and protective film 75. Resin 80 fills the gaps between the conversion elements 54. In addition, a transparent piezoelectric single crystal is used for each conversion element 54. The electroacoustic conversion unit 23 formed by fixing these materials on a support 72 made of a transparent resin can provide an optically transparent unit. Therefore, light emitted from the irradiation unit 15 can pass through the electroacoustic conversion unit 23 and radiated on the subject 7.

Figure 11:
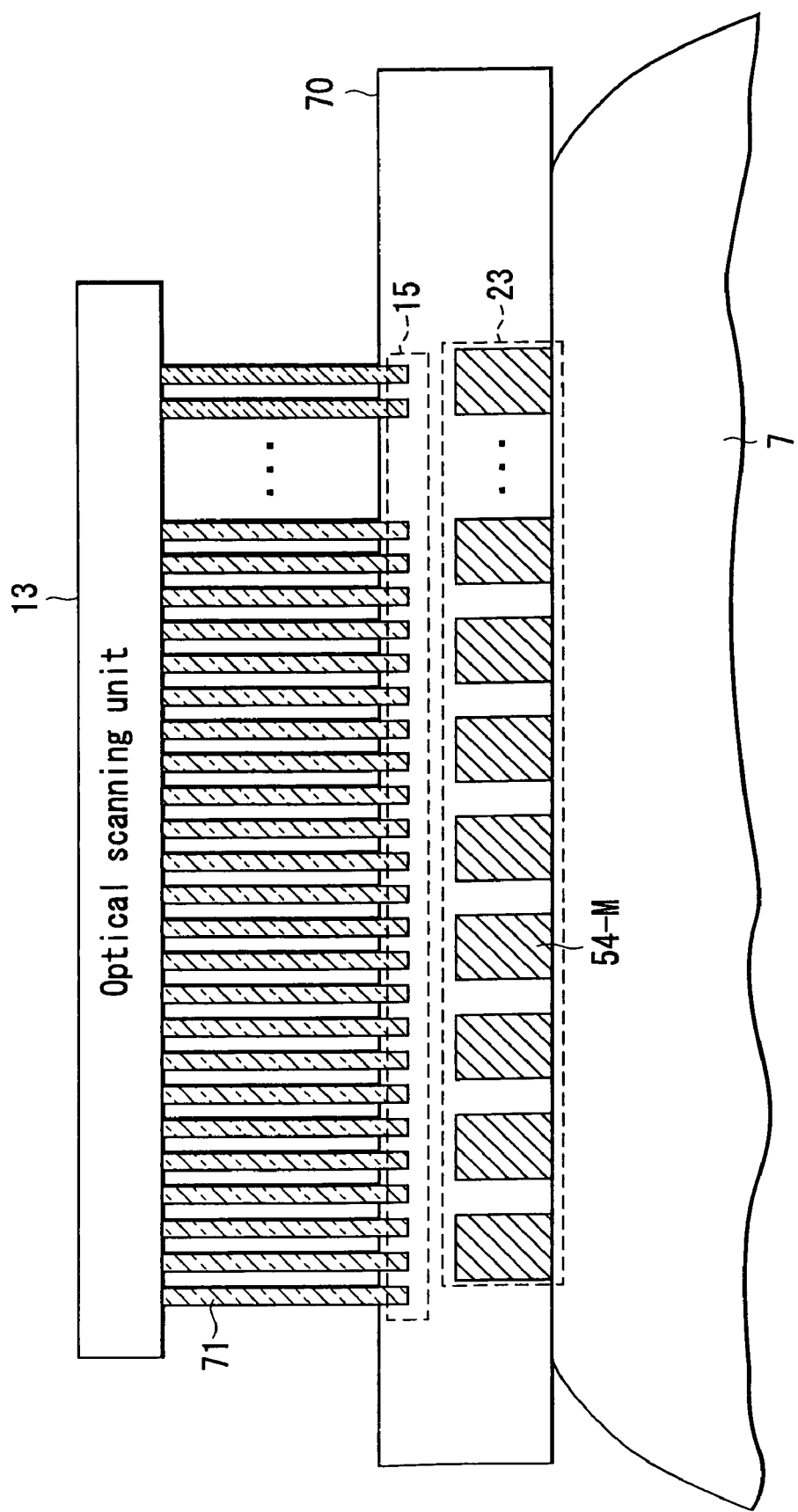
FIG. 11 is a diagram showing a modified applicator according to the fourth embodiment of the present invention.

In the first to third embodiments, the intervals of the optical fibers 71 are determined by the intervals of the conversion elements 54. The fourth embodiment has no such restriction. Optical fibers can be arrayed at a high density as shown in FIG. 11. The intervals of the optical fibers 71 determine scan intervals in photoacoustic imaging. The fourth embodiment can therefore obtain photoacoustic images with a high scan density. The high-density scanning can improve the image quality, particularly if the spatial resolution of an image is determined by the directivity of irradiation light as in the third embodiment.

In the fourth embodiment, the irradiation unit 15 can be placed behind the electroacoustic conversion unit 23. Therefore, the acoustic coupling in the conversion elements 54 can decrease. This renders it possible to obtain good photoacoustic images and good pulse echo images.

In addition, the spatial resolution of photoacoustic images can be improved since the optical fibers 71 are arranged at a high density.

Fifth Embodiment:

In the first to fourth embodiments, the optical scanning unit 13 moves the irradiation position on the subject 7, by sequentially selecting the plurality of arrayed optical fibers 71. This method requires using many optical fibers 71 in the waveguide unit 14 and using the optical scanning unit 13 for selecting the fibers 71. The apparatus must inevitably complicated.

The fifth embodiment has been designed to solve this problem in providing irradiation light. Irradiation light in the photoacoustic imaging method has almost homogeneous properties over a wide range. The spatial resolution of a photoacoustic image is determined by the convergence of acoustic waves in conversion elements 54. The fifth embodiment employs the same method of receiving acoustic waves as in the first embodiment.

Figure 12A:
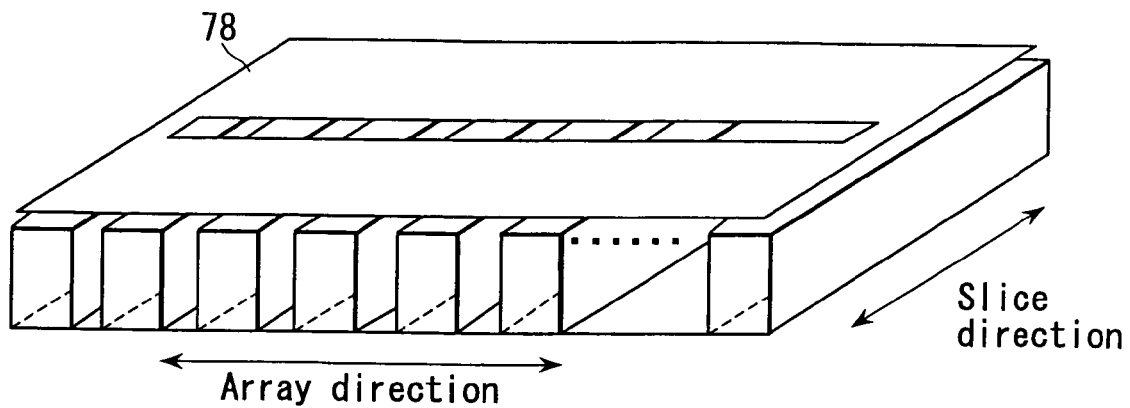
FIGS. 12A and 12B are diagrams explaining an irradiation method using a slit, according to the fifth embodiment of the present invention.
Figure 12B:
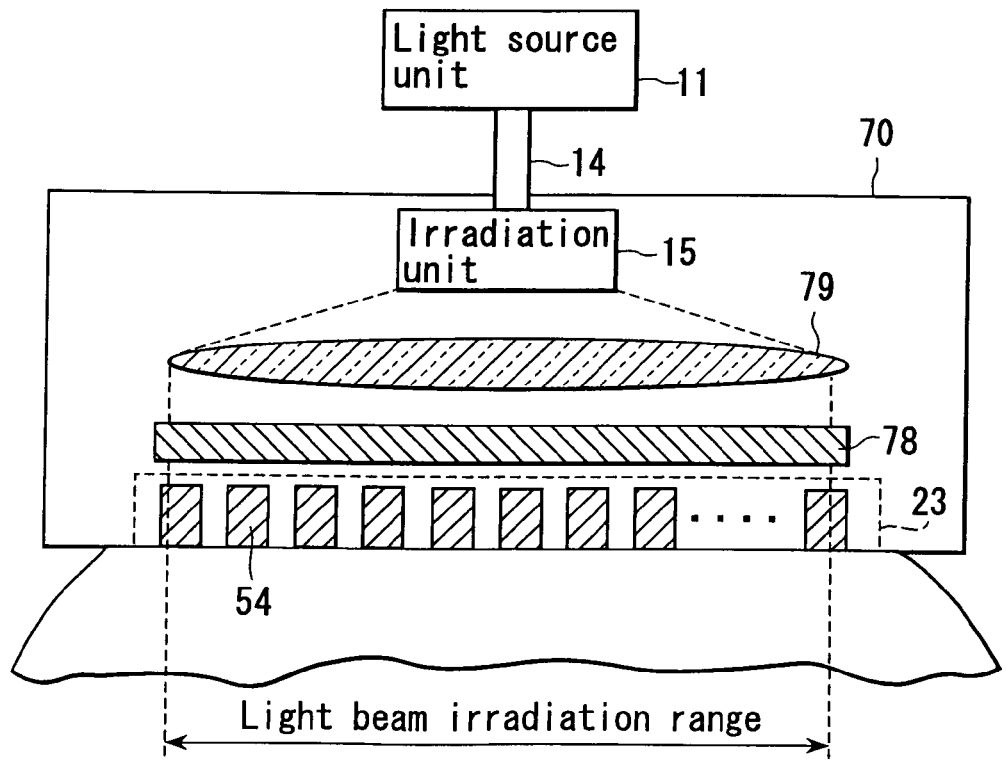
Figure 14:
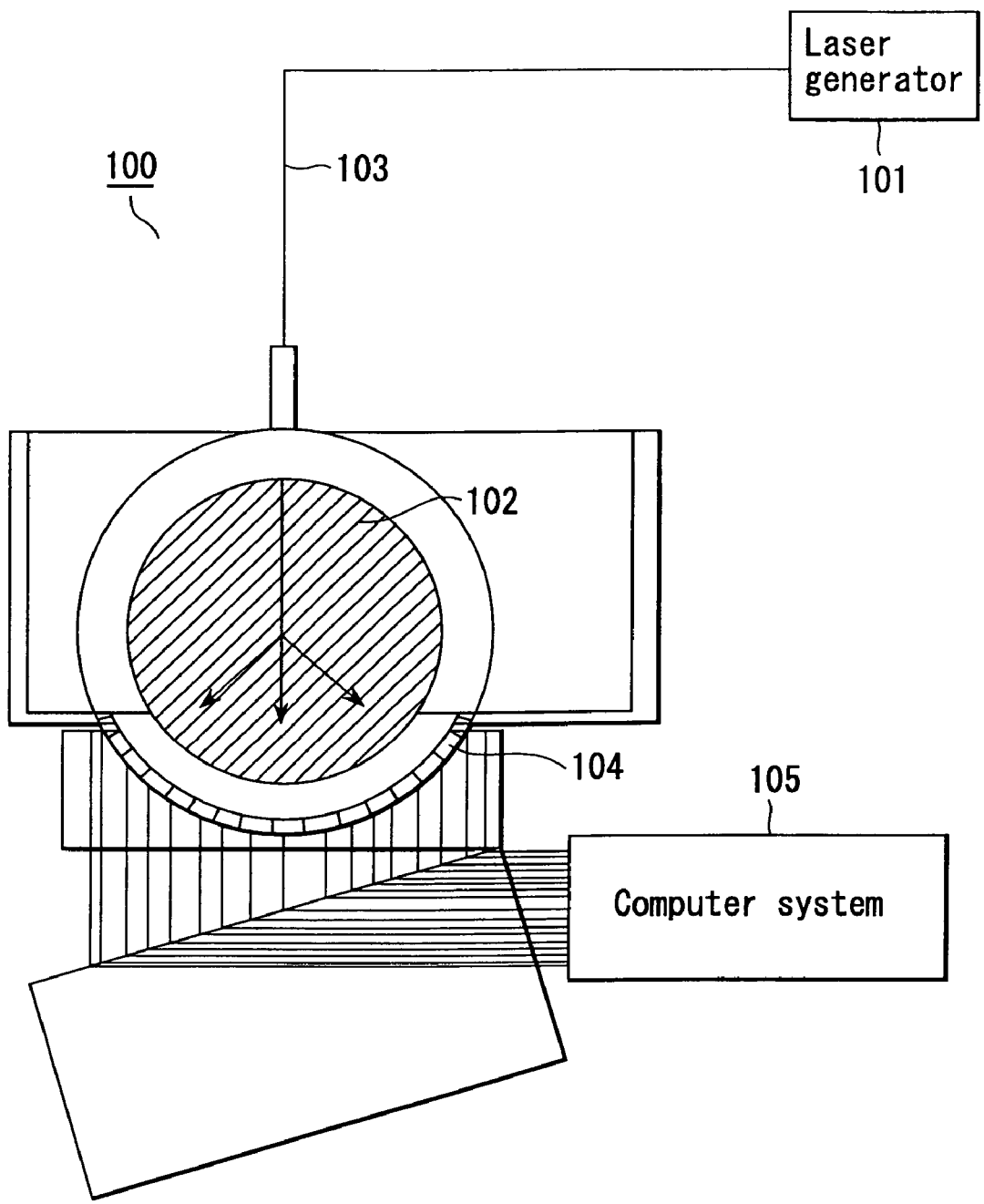
FIG. 14 is a diagram showing a conventional system for acquiring photoacoustic image data.

The method of forming irradiation light in the fifth embodiment will be outlined, with reference to FIGS. 12A and 12B. FIG. 12A represents the positional relationship between a slit plate 78 and the conversion elements 54. FIG. 12B is a schematic diagram of the applicator 70 used in the embodiment. An electroacoustic conversion unit 23 has an optically transparent, like the one utilized in the fourth embodiment.

In the fifth embodiment, the slit plate 78 extends parallel to the array surface of the conversion elements 54 as shown in FIG. 12A. A slit is formed almost in the middle of the plate 78 and extends in the direction the conversion elements 54 are arrayed. The beam of light passing through the slit has a large width in the array direction of the conversion elements 54, and a small width in the slice direction perpendicular to this direction.

The applicator 70 shown in FIG. 12B has a lens 79 in addition to the slit plate 78. The lens 79 converts the divergent light output from an irradiation unit 15 into a parallel beam. A waveguide unit 14 guides the light supplied to the irradiation unit 15, directly from a light source unit 11 or an optical multiplexing unit 12. Hence, the optical scanning unit 13 is unnecessary. The waveguide unit 14 is not limited to optical fibers 71, and one channel may be used as long as sufficient power can be obtained.

A procedure of acquiring photoacoustic image data in this embodiment will be described, with reference to FIGS. 2, 6, 12A and 12B.

The operator operates the operation unit 5, setting imaging conditions for the photoacoustic imaging method and pulse echo method. The operator also sets various conditions concerning the light source, e.g., the wavelength of light to be used for measurement. The data representing these conditions is stored into the internal storage circuit (not shown) of the system control unit 4. After setting the various imaging conditions, the operator places the applicator 70 at a predetermined position on a subject 7. Then, the operation unit 5 is operated for inputting a command to start the acquisition of photoacoustic image data.

Upon receipt of the command, the system control unit 4 reads the conditions concerning the light source, from the storage circuit. The unit 4 then selects, for example, an Nd·YAG laser in the light source unit 11, in accordance with the set conditions. The unit 4 causes the Nd-YAG laser to generate monochromatic light having a wavelength of 1,000 nm. The waveguide unit 14 constituted by, for example, the optical fibers 71, guides the monochromatic light to the irradiation unit 15 of the applicator 70. The light is diffused and emitted from the distal end of the irradiation unit 15. The lens 79 converges the light diffused, changing it to a parallel beam. The parallel beam is applied to the slit plate 78. The beam width of the light, which passes through the slit of the slit plate 78 and propagates in the array direction and slice direction, is set on the basis of the width of the slit in the respective directions.

The light, now having its width reduced in the slice direction as it passes through the slit, passes through the optically transparent electroacoustic conversion unit 23 and is radiated within the light beam irradiation range of the subject 7 shown in FIG. 12B. The hemoglobin in the blood of the subject 7 absorbs this light and generates acoustic waves.

Referring to FIG. 6, conversion elements 54-1 to 54-N (N=6) are selected from conversion elements 54-1 to 54-M in the electroacoustic conversion unit 23 of the applicator 70. The elements 54-1 to 54-M selected receive the acoustic waves generated in the blood vessel existing in a region at a distance L from the subject surface that the applicator 70 contacts. The reception focal length is L for the acoustic reception signals that the conversion elements 54 receive. That is, the system control unit 4 supplies selection information to a conversion-element selection control circuit 68 of a scan control unit 24. The selection information is included in the scan information stored in the storage circuit. The system control unit 4 also supplies delay time information to a beam focusing control circuit 67 of the scan control unit 24. The delay time information corresponds to the reception focal length.

The conversion-element selection control circuit 68 receives the selection information about the conversion elements 54, from the system control unit 4. In accordance with the selection information, the circuit 68 turns on electronic switches 53-1 to 53-N (N=6), selecting the conversion elements 54-1 to 54-6. The conversion element 54-1 to 54-6 convert the acoustic waves generated inside the subject 7, into electrical signals. The electrical signals are supplied via the electronic switches 53 to preamplifiers 55. The preamplifiers 55 amplify the signals to predetermined amplitudes. The signals output from the preamplifiers 55 are input to reception delay circuits 56.

The acoustic reception signal supplied from the conversion element 54-n to the nth reception delay circuit 56 of the N-channel reception delay circuits 56 is delayed by the time of equation (1) that has been presented in conjunction with the first embodiment. If Fo=L, the acoustic reception signals output from the conversion elements 54-1 to 54-6 are delayed by the delay time, providing N (N=6)-channel acoustic reception signals. An adder 57 adds the N-channel acoustic reception signals together. The acoustic waves generated at the position of the distance L can therefore be combined, upon matching their phases on a line (indicated by the dotted line) that is vertical to the conversion element array surface and extends from a middle point between the conversion elements 54-3 and 54-4. Additionally, the dynamic convergence method is also used in the fifth embodiment, to continuously receive signals in a converged state, regardless of depth (distance).

A filter 66 of a signal processing unit 25 removes noise components from the acoustic reception signals obtained by the conversion elements 54-1 to 54-6 and combined by the adder 57. The signal output from the signal processing unit 25 is subjected to amplitude compression in a logarithmic transformation unit 58. The output signal of the unit 58 is detected by an envelope detector 59. An A/D converter 60 converts the signal detected, into a digital signal. The digital signal, or photoacoustic image data, is stored into an image data memory A 61.

After the first scan ends in photoacoustic imaging, the irradiation region of the subject 7 is irradiated with a parallel beam applied through the lens 79 and slit plate 78, in the same manner as in the first scan. New acoustic waves are generated inside the subject 7 thus irradiated. The conversion element selection control circuit 68 turns on the electronic switches 53-2 to 53-7 in accordance with the selection information about the conversion elements 54 that has been supplied from the system control unit 4. The conversion elements 54-2 to 54-7 are thereby selected as the conversion elements 54 for reception. As in the first scan, the conversion elements 54-2 to 54-6 are connected to preamplifiers 55-2 to 55-6 by the electronic switches 53-2 to 53-6 and to reception delay circuits 56-2 to 56-6. The conversion element 54-7 is connected to the preamplifier 55-1 by the electronic switch 53-7 and to the reception delay circuit 56-1.

Here after #1 to #5 are assigned to the reception delay circuits 56-2 to 56-6, which receives reception signals from the conversion elements 54-2 to 54-6, "#1 circuit" to "#5 circuit), and #6 is assigned to the reception delay circuit 56-1, which receive a reception signal from the conversion element 54-7, "#6 circuit". The #n reception delay circuits 56 delay the reception signals from the conversion elements 54, by the delay times given by equation (1). The adder 57 adds and combines the signals delayed by the #n reception delay circuits 56. As in the first scan, the dynamic convergence method can be used to continuously receive acoustic waves generated inside the subject 7 in a converged state, regardless of depth. After the N (N=6)-channel acoustic reception signals obtained by the conversion elements 54-1 to 54-6 are delayed by the delay times, they are added by the adder 57. Thus, the acoustic waves generated on a line (indicated by the dotted line), which is vertical to the surface of the conversion-element array and which extends from a middle point between the conversion elements 54-4 and 54-5, are combined into one signal, while being matched in their phases.

The acoustic reception signal output from the adder 57 is subjected to noise removal in the filter 66, to amplitude compression in the logarithmic transformation unit 58, and to envelope detection in the envelope detector 59. The output signal of the detector 59 is supplied to the A/D converter 60. The A/D converter 60 converts the signal to a digital signal. The digital signal, or photoacoustic image data, is stored into the image data memory A 61.

The third and subsequent scans are performed in the same manner. The system control unit 4 receives the acoustic signals generated from parallel light applied to the subject 7 by the conversion elements 54-3 to 54-8, 54-4 to 54-9, . . . , and 54-M-5 to 54-M. The 6-channel reception signals are sequentially stored as photoacoustic image data into the image data memory A 61 via the preamplifiers 55, reception delay circuits 56, filter 66, logarithmic transformation unit 58, envelope detector 59, and A/D converter 60. Thus, one-frame acoustic image data is obtained.

The pulse echo method is then performed to acquire image data. The procedure of acquiring image data by means of the pulse echo method is the same as in the first embodiment. The procedure will not be described.

In the fifth embodiment, the number of optical fibers 71 in the waveguide unit 14 can be greatly reduced, and the optical scanning unit 13 need not be used. Additionally, the scan density can be arbitrarily set when the delay time is set immediately before the reception, because the irradiation light is continuously applied in the array direction. Therefore, no restrictions are imposed on the optical fibers 71 used.

In the fifth embodiment, the reception convergence point is set on a line vertical to the array surface of conversion elements. Nonetheless, the convergence point can be set at a different position by controlling the delay time for the reception signals that the conversion elements 54 generate.

A modification of the scanning method employed in the fifth embodiment will be descried, with reference to FIGS. 13A to 13C. As indicated above, the image data is acquired, frame by frame, in the fifth embodiment. Instead, image data can be acquired, scan by scan. For example, the pulse echo method may perform scanning in the first direction, after the photoacoustic imaging method finishes scanning in the first direction, and then the photoacoustic imaging method may carries out scanning in the second direction by. As described above, the photoacoustic image data is acquired in one step, and the pulse echo image data is acquired in another step, in the fifth embodiment. Nevertheless, the photoacoustic image data and the ultrasonic image data may be simultaneously acquired by synchronizing the optical pulses with the rate pulses. Note that the optical signals have been generated by the light source unit 11 of the optical transmission unit 1, from a control signal supplied from the system control unit 4. Also note that the rate pulses have been generated by the rate signal-generating unit 21 of the image data-generating unit 2.

FIGS. 13A to 13C are diagrams representing the difference between the scanning sequences described above. FIG. 13A shows a scanning method performed on a frame period, as in the first embodiment. FIG. 13B shows a scanning method carried out on a scan basis. FIG. 13C shows the scanning sequences performed in the photoacoustic imaging method and pulse echo method, to achieve simultaneous scanning. In the simultaneous scanning, scanning is carried out in the α direction (θ1 to θ2) to generate both photoacoustic image data and ultrasonic image data.

In the frame-basis scanning method of FIG. 13A, the scanning is performed first α times in θ1 to θα directions to acquire one-frame photoacoustic image data, and then performed α times to acquire ultrasonic image data. By contrast, in the scan basis-scanning method of FIG. 13B, the scanning is performed first in the θ1 direction to acquire photoacoustic image data, and then in the θ1 direction to acquire ultrasonic image data. Furthermore, the scanning is carried out in the θ2 direction to acquire photoacoustic image data. In the scan-basis scanning method, even an organ moving fast or the blood can be measured in the same phase. This is because the difference in acquisition timing between data in a predetermined direction is greatly reduced.

FIG. 13D shows a modification of the method shown in FIG. 13A. To increase the amount of light transmitted to improve the reception sensitivity in photoacoustic imaging, the irradiation must be repeated less times over a unit time to ensure the safety of the subject. To this end, the scanning is repeated less times over a unit time in the photoacoustic imaging method, than in the pulse echo method.

In the method shown in FIG. 13C, the scanning is carried out simultaneously in the photoacoustic imaging method and in the pulse echo method. Thus, photoacoustic image data is acquired in the photoacoustic imaging method, at the same time ultrasonic image data is acquired in the pulse echo method. Thus, any target that moves fast can be measured more accurately than by the scan-basis scanning method described above. In this simultaneous scanning method, the acoustic waves processed in the photoacoustic imaging method may have the same frequency as the ultrasonic waves from which images are generated in the pulse echo method. If this is the case, the photoacoustic image data and the ultrasonic image data are received as soon as they are mixed. Hence, they cannot be displayed in different colors so that they may be distinguished from each other. Nonetheless, both image data memories A 61 and B 62 can be dispensed with, because an output from the A/D converter 60 of the signal processing unit 25 can be directly stored in the display image memory 63. In addition, the photoacoustic image data and the ultrasonic image data need not be combined.

The images obtained by the photoacoustic imaging method and pulse echo method are identified and displayed in the simultaneous scanning method, by using dual-frequency probes as the conversion elements 54 of the electroacoustic conversion unit 23. This two-frequency probe comprises two conversion elements 54 that differ in thickness to receive two ultrasonic waves of different frequencies, as is disclosed in Jpn. Pat. Appln. KOKAI Publication Nos. 61-100237 and 62-39761.

Therefore, photoacoustic image data and ultrasonic image data can be independently generated and discriminated by the filter 66 of the signal processing unit 25, if the acoustic wave in the photoacoustic imaging method and ultrasonic wave in the pulse echo method have frequency of 1.5 MHz and the frequency of 3 MHz, respectively, even when they are simultaneously received by the conversion element 54. In addition, these image data items can be identified by colors and displayed on the CRT monitor 65 of the display unit 6.

Figure 15A:
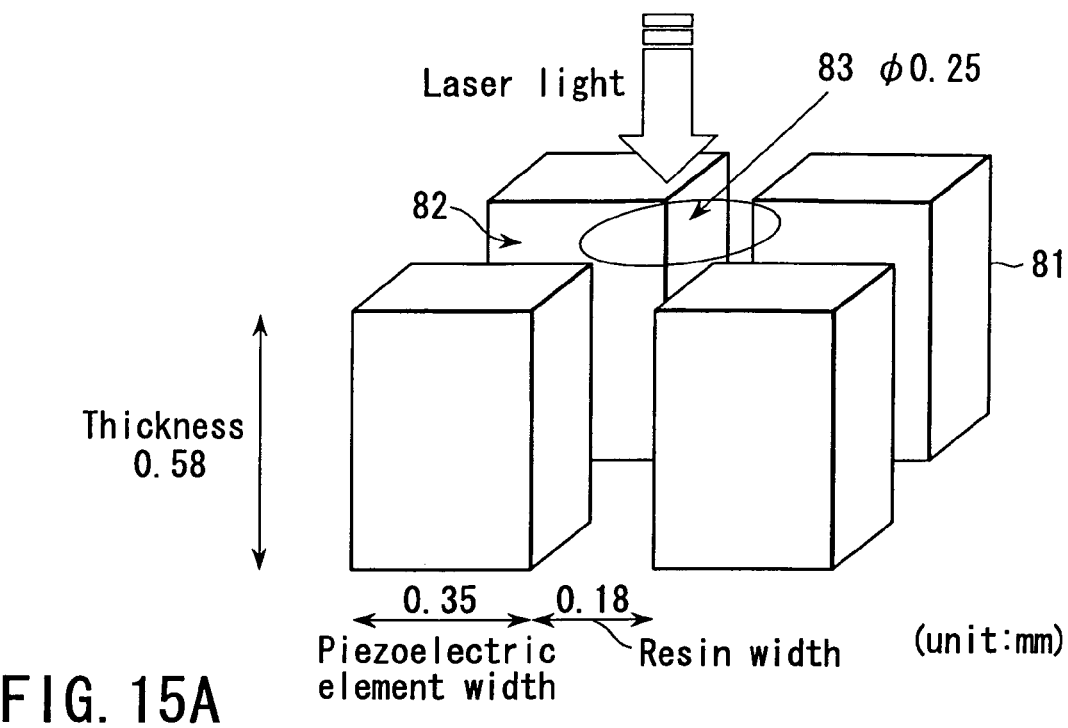
FIGS. 15A and 15B are perspective views, each showing the outer appearance of part of an electroacoustic conversion unit according to the sixth embodiment of the invention.
Figure 15B:
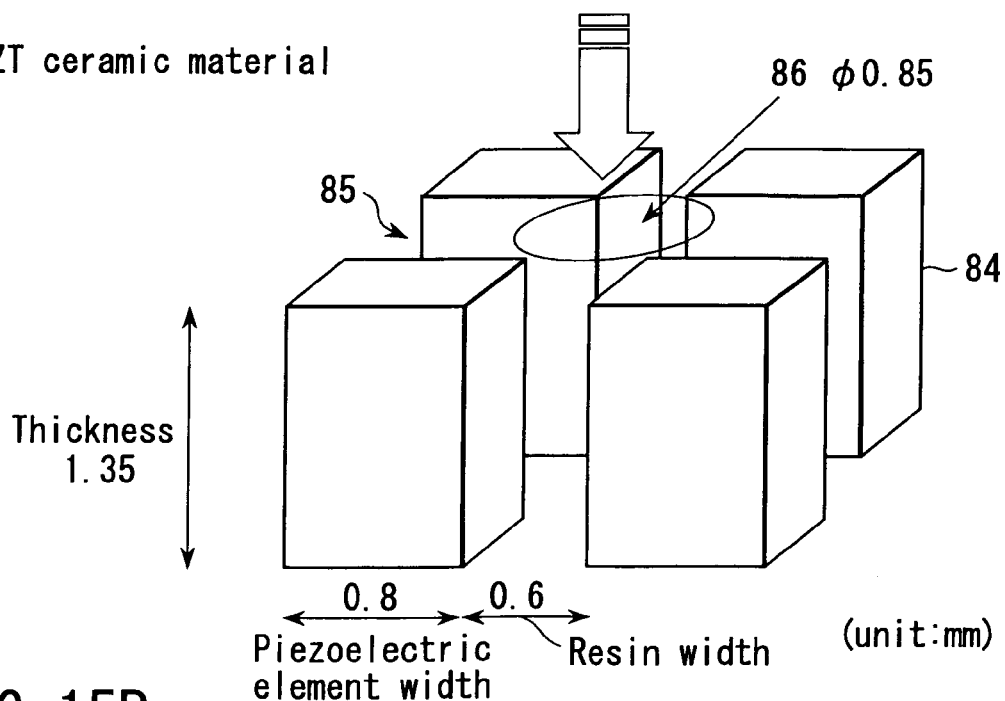
Figure 16:
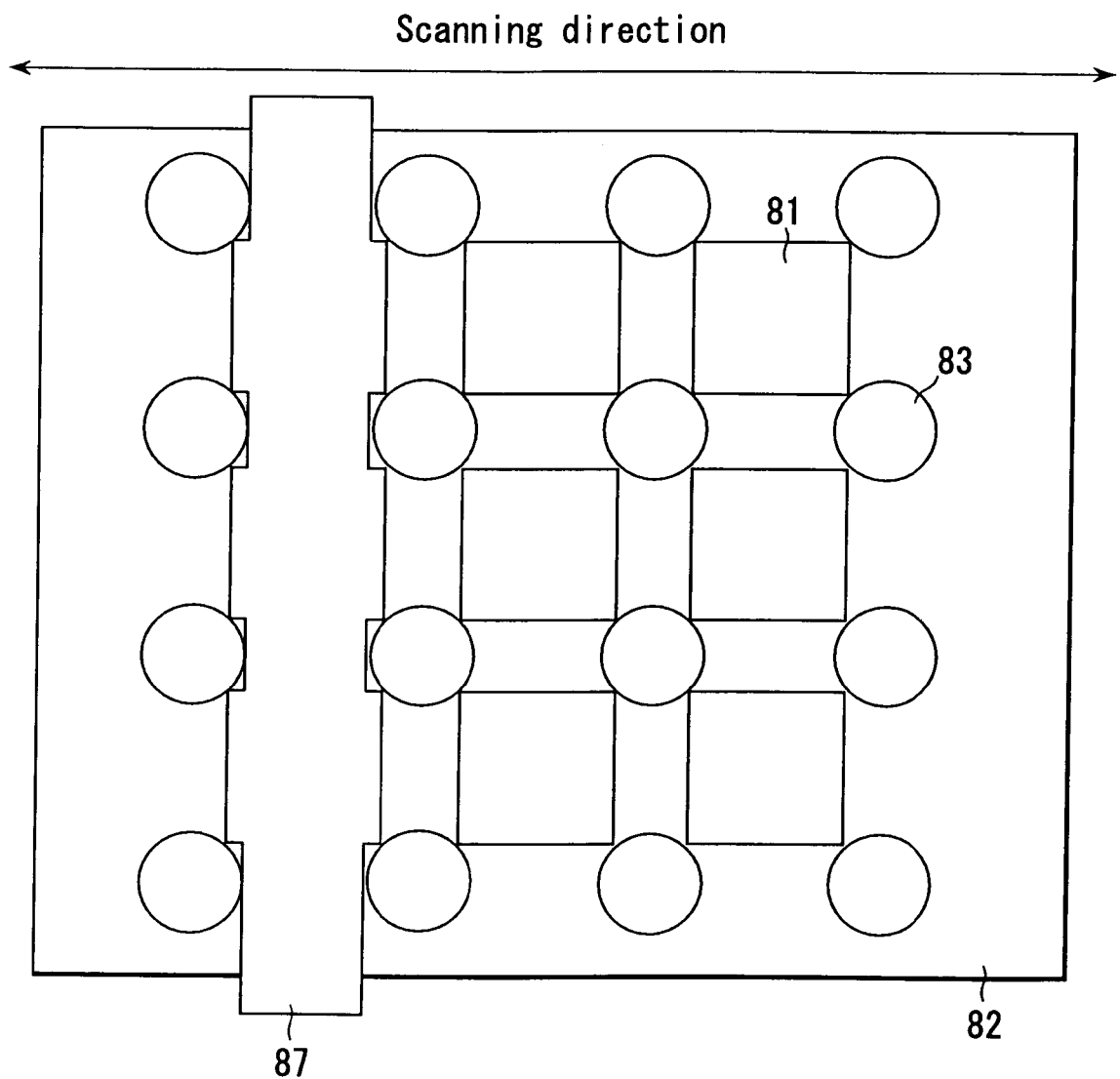
FIG. 16 is a plan view showing part of the electroacoustic conversion unit shown in FIG. 14.

Sixth Embodiment:

The sixth embodiment of the invention relates to the electroacoustic conversion unit used in the above embodiment. FIGS. 15A and 15B show the outer appearances of electroacoustic conversion units according to the sixth embodiment. FIG. 16 is a plan view of the electroacoustic conversion unit shown in FIG. 15A. FIG. 15A depicts a conversion unit that has a PZNT single-crystal with light transmission property for a piezoelectric element of each conversion element. FIG. 15B illustrates a conversion unit that comprises a PZT ceramic material having no light transmission property for a piezoelectric element of each conversion element.

As FIG. 15A shows, a plurality of piezoelectric elements 81, each having a light transmission property, are arranged at predetermined intervals in the form of a matrix (two-dimensionally). A short optical fiber used as an optical path 83 is placed in each space surrounded by four adjacent piezoelectric elements 81. Instead, the optical path 83 may be placed between two piezoelectric elements 81 that are adjacent in the scanning direction. The gap between each piezoelectric element 81 and the optical path 83 is filled with resin 82 that has a light transmittance higher than that of the piezoelectric elements 81, but lower than that of an optical fiber. When the resin 82 is cured, the electroacoustic conversion unit is integrated.

Assume that the center frequency is 1 MHz. Then, each piezoelectric element 81 is a rectangular parallelepiped, 0.35 mm wide and 0.58 mm long. The piezoelectric elements 81 are arranged at 0.18-mm intervals. In this case, the optical path 83, for example, has a diameter of 0.25 mm.

As FIG. 16 shows, a single electrode pattern 87 that has a light transmission property is commonly formed for all piezoelectric elements 81 arranged in a line perpendicular to the scanning direction. The piezoelectric elements 81 are connected to one electrode pattern 87, constituting a piezoelectric vibrator.

Optical fibers 71 are connected to the optical paths 83 with an optical adhesive. The light guided through the optical fibers 71 is applied to a subject through the optical paths 83. Note that the piezoelectric elements 81 and resin 82 can transmit light. That is, the electroacoustic conversion unit is made of material that can transmit light. Hence, any one of the structures shown in FIGS. 9 to 12 can be used, without connecting the optical fibers 71 to the optical paths 83 to output light through the optical paths 83.

Figure 17A:
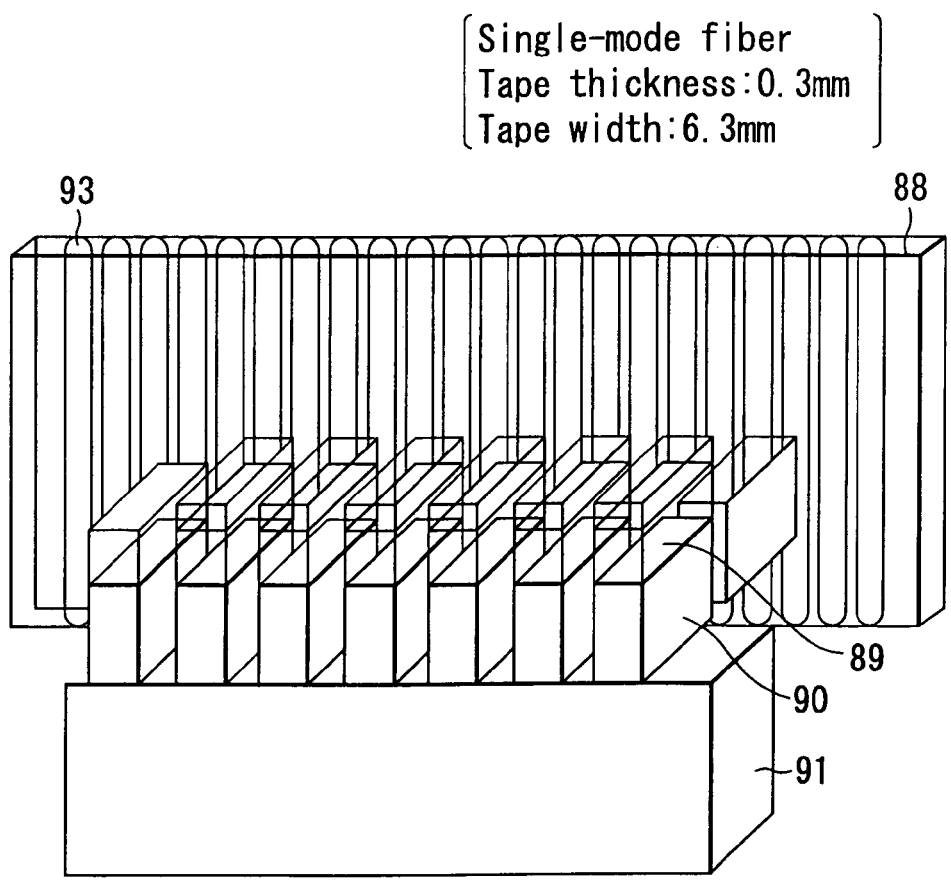
FIGS. 17A and 17B are diagrams depicting an electroacoustic conversion unit according to the seventh embodiment of the present invention.
Figure 17B:
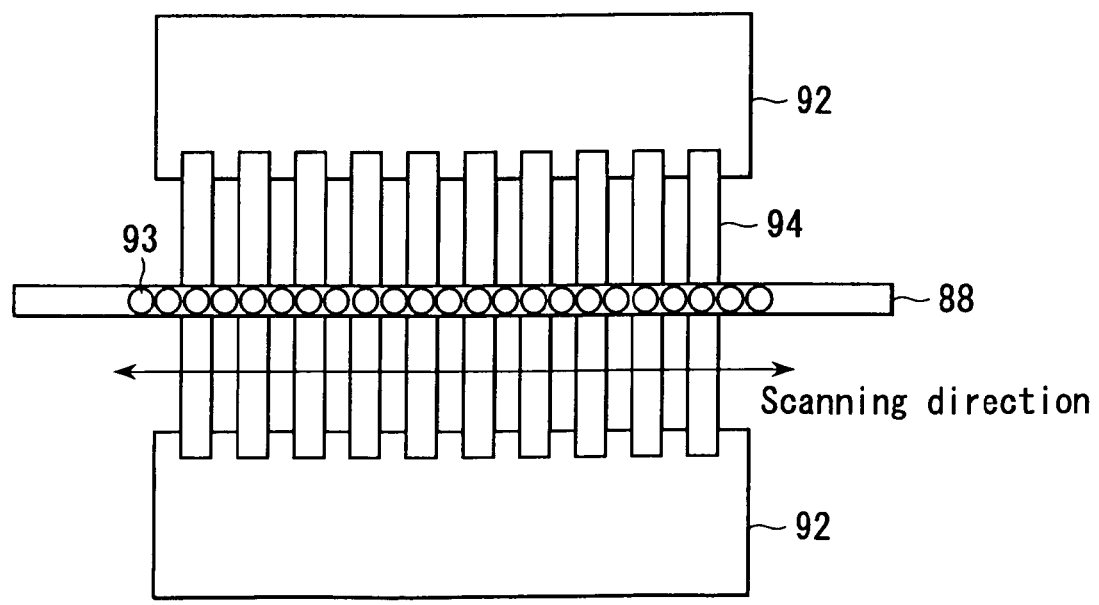

Seventh Embodiment:

The seventh embodiment of this invention relates to the electroacoustic conversion unit used in the embodiment described above. FIGS. 17A and 17B show the outer appearance of an electroacoustic conversion unit according to the seventh embodiment. A multi-type optical fiber tape 88 is used for an electroacoustic conversion unit according to this embodiment. The tape 88 comprises a tape member and a plurality of optical fibers 93 regularly arranged on the tape member at predetermined intervals. A plurality of piezoelectric elements 90 made of PZNT or PZT are arrayed in a line. Electrodes are formed on the upper and lower surfaces of each piezoelectric element 90, whereby a piezoelectric vibrator is formed.

An acoustic matching layer 89 is bonded to the front of each vibrator. A backing material 91 is bonded to the rear surfaces of all vibrators. The arrayed electrodes of vibrators are mounted on a flexible circuit (FPC) 92 and extend perpendicular to the array. Two vibrator arrays 94 are bonded to each other by the multi-type optical fiber tape 88.

Having optical fibers, the use of this multi-type optical fiber tape 88 facilitates the manufacturing of an electroacoustic conversion unit that has light transmission property.

Figure 18A:
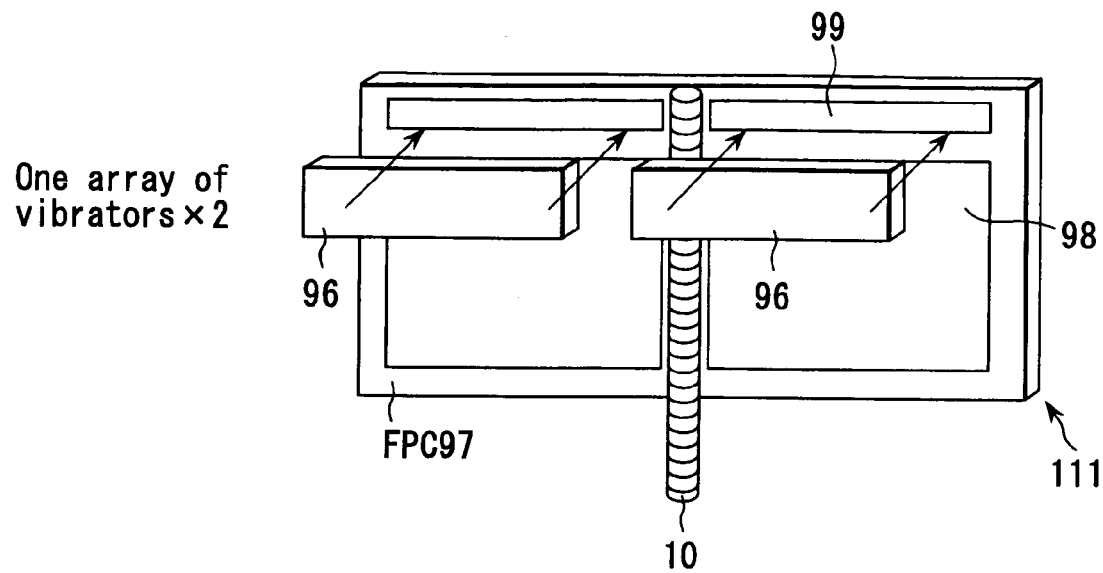
FIGS. 18A and 18B are perspective views showing the arrangement of an electroacoustic conversion unit according to the eighth embodiment of the present invention.
Figure 18B:
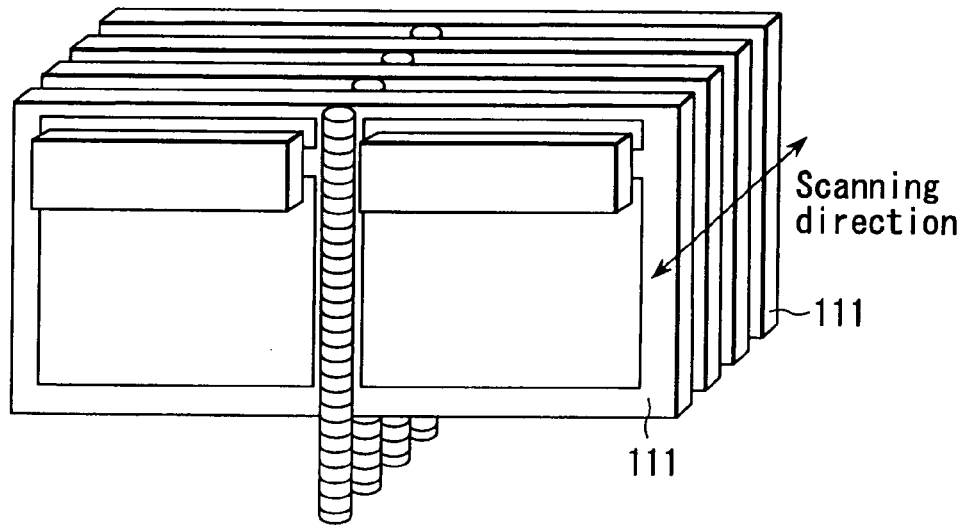

Eighth Embodiment:

The eighth embodiment of the invention relates to the electroacoustic conversion unit used in the above embodiment. FIGS. 18A and 18B show the outer appearance of an electroacoustic conversion unit according to the eighth embodiment. As FIG. 18A illustrates, signal-side electrodes 98 are formed on two sides of a substantially middle portion of a flexible circuit (FPC) 97 that is 0.05 mm thick. A pair of ground-side electrodes 99 are formed on the two sides of the substantially middle portion. An optical fiber 110 having a diameter of, for example, 0.2 mm is bonded to the substantially middle portion of the flexible printed board 97. The signal-side electrode and ground-side electrode of a piezoelectric viblator (transducer) 96, which has a PZNT or PZT material, are formed by sputtering Au or the like and electrically connected to the signal-side electrode 98 and ground-side electrode 99 provided on one side of the optical fiber 110. Likewise, the signal-side electrode and ground-side electrode of a vibrator 96 are formed by sputtering Au or the like and electrically connected to the signal-side electrode 98 and ground-side electrode 99 provided on the other side of the optical fiber 110.

Transducer units 111, each thus configured, are stacked on each other in the scanning direction. They are bonded together with an adhesive, as shown in FIG. 18B.

In this embodiment, an electroacoustic conversion unit having a light transmission property can be easily manufactured by using optical fibers as in the seventh embodiment.

The embodiments of the present invention have been described above. Nevertheless, the invention is not limited to the embodiments. Rather, it can be modified. In the embodiments described above, the conversion elements 54 of the electroacoustic conversion unit 23 and the optical fibers 71 of the irradiation unit 15 are arranged in the form of flat arrays. Instead, they may be arranged to form convex or concave arrays.

In the embodiments, a photoacoustic image and an ultrasonic image are superimposed and displayed on the display unit 6. If a photoacoustic image composed of the two images superimposed may jeopardize the observation of an acoustic image, these two images may be displayed side by side.

In addition, the above embodiments exemplify the method of acquiring photoacoustic image data and ultrasonic image data, which is started when the operator inputs an acquisition start command. Instead, the acquisition of ultrasonic image data may be automatically started at the end of acquisition of photoacoustic image data. Furthermore, the respective image data items are acquired for each frame in the above embodiments, but they may be acquired for each scan. For example, the first scan by the pulse echo method may be performed when the first scan is completed in the photoacoustic imaging method. In this case, the second scan may be performed in the photoacoustic imaging method. The order of these scans may be reversed.

In the present invention, the display range of a photoacoustic image need not be matched with that of an ultrasonic image. For example, an area where the distribution of a specific substance is displayed in a photoacoustic image can be displayed in detail by an acoustic image. An operation control unit may be used to select this area in accordance with an instruction signal the operator has input by operating the operation unit 5.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for diagnosing breast cancer in humans that comprises the steps of:
   a. Bringing a diagnostic probe in touch with breast tissue, said diagnostic probe further comprises an ultrasound imaging elements and photo-acoustic illumination and detection elements,
   b. Illuminating said breast tissue with short duration light pulses having wavelengths that lie in the absorption spectral bands of hemoglobin, to generate photoacoustic signals,
   c. detecting said photoacoustic signal using ultrasound transducers to determine the distribution of blood (vascularization) of breast tissue,
   d. generating and detecting an ultrasound image of the morphology of said human breast tissue, using ultrasound transducers that are co-registered with said photo-acoustic detection transducers used in the detection of said photo acoustic signals; and
   e. Overlaying said photo acoustic vascularization image over said ultrasound morphology image to generate a combined image of the vascular distribution in different morphological structures in the breast, said morphological structure are the lesions of interest.

2. The method of claim 1, wherein the wavelengths of light are in the spectral range between 530 nm and 1300 nm.

3. The method of claim 1, wherein the photo acoustic detection elements and the ultrasound detection elements are common.

4. The method of claim 1, wherein the ultrasound transducers are piezoelectric elements.

5. The method of claim 1, wherein the ultrasound transducers are PZNT elements.

6. The method of claim 1, wherein the ultrasound transducers are PVDF elements.

7. The method of claim 1, wherein, the combined photoacoustic detection elements and the ultrasound detection elements are impedance matched to the skin to minimize ultrasound reflection loss.

8. The method of claim 1, wherein coupling gel is applied to the detector elements.

9. An apparatus for diagnosing disease such as breast cancer in humans by superimposing a distribution of the concentration of an analyte, such as hemoglobin over imaged morphological features such as lesions, said apparatus comprising:
   a. Light generating unit, which generates light containing a specific wavelength component;
   b. An irradiation unit, which radiates the light generated by the light-generating unit into a subject to be examined;
   c. Wave guide means for guiding the light generated by the light-generating unit to the irradiation unit;
   d. First electroacoustic conversion means for converting acoustic waves generated in the subject by the light radiated by the irradiation unit into electrical signals by using a plurality of arrayed electroacoustic transducer elements;

e. First image data generating means for generating first image data on the basis of the signals obtained by the first electroacoustic conversion means;
f. Ultrasonic wave transmission means for transmitting ultrasonic waves into the subject;
g. Second electroacoustic conversion means for converting components of the ultrasonic waves transmitted by the ultrasonic wave transmission means which are reflected inside the subject into electrical signals by using a plurality of arrayed electroacoustic transducer elements;
h. Second image data generating means for generating second image data on the basis of the signals obtained by the second electroacoustic conversion means; and
i. Display means for displaying the first image data and the second image data.

10. A subject-information imaging apparatus for the determination distribution of the concentration of an analyte, over imaged morphological features in tissue, said apparatus comprising:
a light generating unit which generates light containing a specific wavelength component;
an irradiation unit which radiates the light generated by the light generating unit into a subject to be examined;
waveguide means for guiding the light generated by the light generating unit to the irradiation unit;
first electroacoustic conversion means for converting acoustic waves generated in the subject by the light radiated by the irradiation unit into electrical signals by using a plurality of arrayed electroacoustic transducer elements;
first image data generating means for generating first image data on the basis of the signals obtained by the first electroacoustic conversion means;
ultrasonic wave transmission means for transmitting ultrasonic waves into the subject;
second electroacoustic conversion means for converting components of the ultrasonic waves transmitted by the ultrasonic wave transmission means which are reflected inside the subject into electrical signals by using a plurality of arrayed electroacoustic transducer elements;
second image data generating means for generating second image data on the basis of the signals obtained by the second electroacoustic conversion means; and
display means for displaying the first image data and the second image data.

11. An apparatus according to claim 10, wherein at least one of said plurality of electroacoustic transducer elements of the first electroacoustic conversion means is commonly used as one of said plurality of electroacoustic transducer elements of the second electroacoustic conversion means.

12. An apparatus according to claim 10, wherein the waveguide means is constituted by a plurality of optical fibers, and end portions of the optical fibers on one side are arrayed and open at the irradiation unit.

13. An apparatus according to claim 12, wherein said plurality of electroacoustic transducer elements of the first and second electroacoustic conversion means are arrayed in substantially the same direction as an array direction of said plurality of optical fiber opening portions.

14. An apparatus according to claim 13, wherein said plurality of optical fiber opening portions and said plurality of electroacoustic transducer elements are arrayed one-dimensionally.

15. An apparatus according to claim 13, wherein said plurality of optical fiber opening portions and said plurality of electroacoustic transducer elements are arrayed two-dimensionally in substantially the same plane.

16. An apparatus according to claim 13, wherein said plurality of optical fiber opening portions are arranged in gaps formed when the electroacoustic transducer elements are arrayed.

17. An apparatus according to claim 10, wherein the first electroacoustic conversion means converts the acoustic waves into electrical signals by selecting and using a plurality of adjacent electroacoustic transducer elements of said plurality of electroacoustic transducer elements.

18. An apparatus according to claim 17, wherein the first image data generating means performs phased addition of a plurality of electrical signals obtained by the electroacoustic transducer elements selected by the first electroacoustic conversion means.

19. An apparatus according to claim 12, further comprising optical scanning means for selecting a predetermined optical fiber from said plurality of optical fibers and supplying light to the irradiation unit.

20. An apparatus according to claim 19, wherein a middle position between a plurality of electroacoustic transducer elements selected by the first electroacoustic conversion means substantially coincides with an opening position of an optical fiber selected by the optical scanning means at the irradiation unit.

21. An apparatus according to claim 10, wherein the electroacoustic transducer elements of the first and second electroacoustic conversion means are formed from a piezoelectric single crystal.

22. An apparatus according to claim 10 or 21, wherein the electroacoustic transducer elements are arranged between the irradiation unit and the subject, and light output from the irradiation unit is transmitted through the electroacoustic transducer elements and radiated on the subject.

23. An apparatus according to claim 13, wherein an array density of said plurality of optical fiber opening portions in the irradiation unit is higher than an array density of said plurality of electroacoustic transducer elements.

24. An apparatus according to claim 22, further comprising an optical lens between the irradiation unit and said plurality of arrayed electroacoustic transducer elements, the optical lens setting a spot size of light output from the irradiation unit to a predetermined width in the array direction of the electroacoustic transducer elements.

25. An apparatus according to claim 24, further comprising a slit plate between the optical lens and the electroacoustic conversion element, the slit plate setting a beam width of light output from the optical lens in a slice direction perpendicular to the array direction of the electro acoustic transducer elements.

26. An apparatus according to claim 10, wherein the second image data generating means generates image data by extracting harmonic components from reception signals acquired by the second electroacoustic conversion means.

27. An apparatus according to claim 10, wherein irradiation of light from the irradiation unit for generation of the first image data and transmission of ultrasonic waves from the ultrasonic wave transmission means for generation of the second image data are alternately performed.

28. An apparatus according to claim 27, wherein irradiation of light from the irradiation unit and transmission of ultrasonic waves from the ultrasonic wave transmission means are alternately performed in each of a plurality of directions.

29. An apparatus according to claim 10, wherein after the first image data corresponding to one frame is generated by making the irradiation unit sequentially radiate light in a plurality of directions, the ultrasonic wave transmission means generates the second image data corresponding to one frame by sequentially transmitting ultrasonic waves in the plurality of directions.

30. An apparatus according to claim 10, wherein irradiation of light from the irradiation unit for generation of the first image data and transmission of ultrasonic waves from the ultrasonic wave transmission means for generation of the second image data are performed substantially simultaneously.

31. An apparatus according to claim 10, wherein the display means displays the first and second image data on the same monitor.

32. An apparatus according to claim 10 or 31, wherein the display means superimposes/displays the first and second image data.

33. An apparatus according to claim 10, wherein the display means displays the first and second image data in different colors.

34. An apparatus according to claim 10, wherein the irradiation unit generates light substantially at the same time when the ultrasonic transmission means generates ultrasonic waves.

35. An apparatus according to claim 10, wherein the first electroacoustic conversion means, the ultrasonic wave transmission means, and the second electroacoustic conversion means are commonly formed as piezoelectric vibrators, said plurality of piezoelectric vibrators are arranged at predetermined intervals in the form of a matrix, and optical paths are formed in gaps between the piezoelectric vibrators.

36. An apparatus according to claim 10, wherein the first electroacoustic conversion means, the ultrasonic wave transmission means, and the second electroacoustic conversion means are commonly formed as piezoelectric vibrators, and said plurality of piezoelectric vibrators are arranged in a line on each of two sides of a multi-type fiber tape.

37. An apparatus according to claim 10, wherein the first electroacoustic conversion means, the ultrasonic wave transmission means, and the second electroacoustic conversion means are commonly formed as piezoelectric vibrators, the pair of piezoelectric vibrators are bonded to a flexible printed board, together with an optical fiber, to form a vibrator plate, and said plurality of vibrator plates are stacked on each other and integrally boded to each other with an adhesive.

38. A subject-information imaging apparatus for the determination distribution of the concentration of a substance, over imaged morphological features in tissue, said apparatus comprising:
    irradiation means for irradiating a subject to be examined with light;
    ultrasonic wave transmission means for transmitting an ultrasonic wave to the subject;
    electroacoustic conversion means for receiving an acoustic wave generated in the subject by the irradiation light or the transmission ultrasonic wave and converting the wave into an electrical signal;
    first image data generating means for receiving an electrical signal output from the electroacoustic conversion means and generating first image data on the basis of an acoustic wave originating from the irradiation light;
    second image data generating means for receiving an electrical signal output from the electroacoustic conversion means and generating second image data on the basis of an acoustic wave originating from the transmission ultrasonic wave; and
    display means for displaying the first and second image data.

39. An apparatus according to claim 38, wherein the ultrasonic wave transmission means is partly commonly used as the electroacoustic conversion means.

40. An apparatus according to claim 38, wherein the display means displays the first and second image data on a single monitor.

41. A subject-information imaging apparatus for the determination distribution of the concentration of a substance, over imaged morphological features in tissue, said apparatus comprising:
    an irradiation unit configured to irradiate a subject to be examined with light;
    an ultrasonic wave transmission unit configured to transmit an ultrasonic wave to the subject;
    an electroacoustic conversion unit configured to receive an acoustic wave generated in the subject by the irradiation light or the transmission ultrasonic wave and to convert the wave into an electrical signal;
    a first image data generating unit configured to receive an electrical signal output from the electroacoustic conversion unit and to generate first image data on the basis of an acoustic wave originating from the irradiation light;
    a second image data generating unit configured to receive an electrical signal output from the electroacoustic conversion unit and to generate second image data on the basis of an acoustic wave originating from the transmission ultrasonic wave; and
    a display unit configured to display the first and second image data.

42. An apparatus according to claim 41, wherein the ultrasonic wave transmission unit is partly commonly used as the electroacoustic conversion unit.

43. An apparatus according to claim 41, wherein the display unit displays the first and second image data on a single monitor.

* * * * *